United States Patent
Weibel et al.

(10) Patent No.: US 10,001,661 B1
(45) Date of Patent: Jun. 19, 2018

(54) BODY-MOUNTABLE DEVICES HAVING AN OPTICAL POLARIZER

(71) Applicant: Verily Life Sciences LLC, Mountain View, CA (US)

(72) Inventors: Douglas Weibel, Madison, WI (US); Babak Parviz, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 168 days.

(21) Appl. No.: 15/193,955

(22) Filed: Jun. 27, 2016

Related U.S. Application Data

(63) Continuation of application No. 14/199,440, filed on Mar. 6, 2014, now abandoned.

(51) Int. Cl.
| | |
|---|---|
| *G02F 1/137* | (2006.01) |
| *G02C 7/04* | (2006.01) |
| *G02C 7/12* | (2006.01) |
| *A61B 5/145* | (2006.01) |
| *A61B 5/00* | (2006.01) |

(52) U.S. Cl.
CPC .......... *G02C 7/049* (2013.01); *A61B 5/14507* (2013.01); *A61B 5/14532* (2013.01); *A61B 5/14546* (2013.01); *A61B 5/6821* (2013.01); *G02C 7/12* (2013.01); *G02F 1/137* (2013.01)

(58) Field of Classification Search
CPC ..... G02C 7/12; G02C 7/04–7/11; G02B 1/08; G02F 1/137
See application file for complete search history.

(56) References Cited

U.S. PATENT DOCUMENTS

| | | |
|---|---|---|
| 4,572,616 A | 2/1986 | Cleverly et al. |
| 5,682,210 A | 10/1997 | Weirich |

(Continued)

FOREIGN PATENT DOCUMENTS

| | | |
|---|---|---|
| EP | 0592768 | 11/1997 |
| WO | 2004064629 A1 | 8/2004 |

(Continued)

OTHER PUBLICATIONS

Hyman, Paul, "If Google Glass is a Hit, Can Contacts Be Far Behind?", Electronics360, Oct. 28, 2013, pp. 1-3. [Retrieved from the Internet Jan. 20, 2014:<URL:http://electronics360.globalspec.com/article/3156/-if-google-glass-is-a-hit-can-contacts-be-far-behind>].

(Continued)

*Primary Examiner* — James Dudek
(74) *Attorney, Agent, or Firm* — McDonnell Boehnen Hulbert & Berghoff LLP

(57) ABSTRACT

A method for preparing a body-mountable device is described. The method involves: forming a first polymer layer, the first polymer layer comprising a first liquid crystal elastomer; positioning a structure on the first polymer layer; and forming a second polymer layer over the first polymer layer and the structure, the second polymer layer comprises a second liquid crystal elastomer, wherein the first polymer layer defines a first side of a body-mountable device and the second polymer layer defines a second side of the body-mountable device opposite the first side, and wherein the application of an electric field across the first polymer layer and the second polymer layer causes the body-mountable device to polarize or depolarize in response to the electric field.

18 Claims, 12 Drawing Sheets

(56) References Cited

U.S. PATENT DOCUMENTS

| | | |
|---|---|---|
| 6,874,888 B1 | 4/2005 | Dudai |
| 7,728,949 B2 | 6/2010 | Clarke et al. |
| 8,038,912 B2 | 10/2011 | Beebe et al. |
| 8,215,770 B2 | 7/2012 | Blum et al. |
| 8,385,998 B2 | 2/2013 | Zhang et al. |
| 8,451,408 B2 | 5/2013 | Chin et al. |
| 8,471,999 B2 | 6/2013 | Valyukh et al. |
| 8,506,740 B2 | 8/2013 | Say |
| 2010/0078838 A1 | 4/2010 | Pugh et al. |
| 2011/0155587 A1 | 6/2011 | Shacham-Diamand et al. |
| 2011/0298794 A1 | 12/2011 | Freedman |
| 2012/0234493 A1 | 9/2012 | Pugh et al. |
| 2013/0243655 A1 | 9/2013 | Li et al. |
| 2015/0077660 A1* | 3/2015 | Pugh .................. G02C 7/04 349/13 |

FOREIGN PATENT DOCUMENTS

| | | |
|---|---|---|
| WO | 2011/130137 A2 | 10/2011 |
| WO | 2011/130138 A1 | 10/2011 |
| WO | 2012122411 A1 | 9/2012 |
| WO | 2013/049000 A1 | 4/2013 |
| WO | 2013/096781 A1 | 6/2013 |

OTHER PUBLICATIONS

Morgan, Erinn, "Polarized Sunglasses: How They Reduce Glare", All About Vision, Apr. 2013, pp. 1-2. [Retrieved from the Internet Jan. 20, 2014:<URL:http://www.allaboutvision.com/sunglasses/polarized.htm>].

"A Bird's Eye View of Liquid Crystal Elastomers", pp. 1-8. [Retrieved from the Internet Mar. 24, 2015:<www.Icelastomer.org.uk/bev>].

"What are Liquid Crystal Elastomers—Polymer Section", p. 1. [Retrieved from the Internet Jan. 16, 2014:<nlcmf.Ici.kent.edu/About_the_NLCMF/whatR1.htm>].

"Liquid Crystal Elastomers", pp. 1-2. [Retrieved from the Internet Jan. 16, 2014:<www.Icelastomer.org.uk>].

"What are Liquid Crystal Elastomers—Mesogen Section", pp. 1-3. [Retrieved from the Internet Feb. 11, 2014: <http://nlcmf.Ici.kent.edu/About_the_NLCMF/whatR_connectivity.htm>].

"Macromolecular Chemistry", Introduction, pp. 1-8. [Retrieved from the Internet Jan. 20, 2014:<www.macromolchem.com/introduction/introduction.htm>].

"Liquid-Crystal Display", Wikipedia, pp. 1-19, dated Jan. 11, 2014. [Retrieved from the Internet Feb. 13, 2014: <URL:http://en.wikipedia.org/wiki/Liquid-crystal_display>].

"Mesogen", Wikipedia, p. 1., dated Apr. 11, 2013. [Retrieved from the Internet Jan. 16, 2014: <URL:http://en.wikipedia.org/wiki/Mesogen>].

Ohm, Christian, et al., "Liquid Crystalline Elastomers as Actuators and Sensors", Advanced Materials, 2010, vol. 22, pp. 3366-3387.

Urayama, Kenji, "Selected Issues in Liquid Crystal Elastomers and Gels", Macromolecules, Apr. 3, 2007, vol. 40(7), pp. 2277-2288.

* cited by examiner

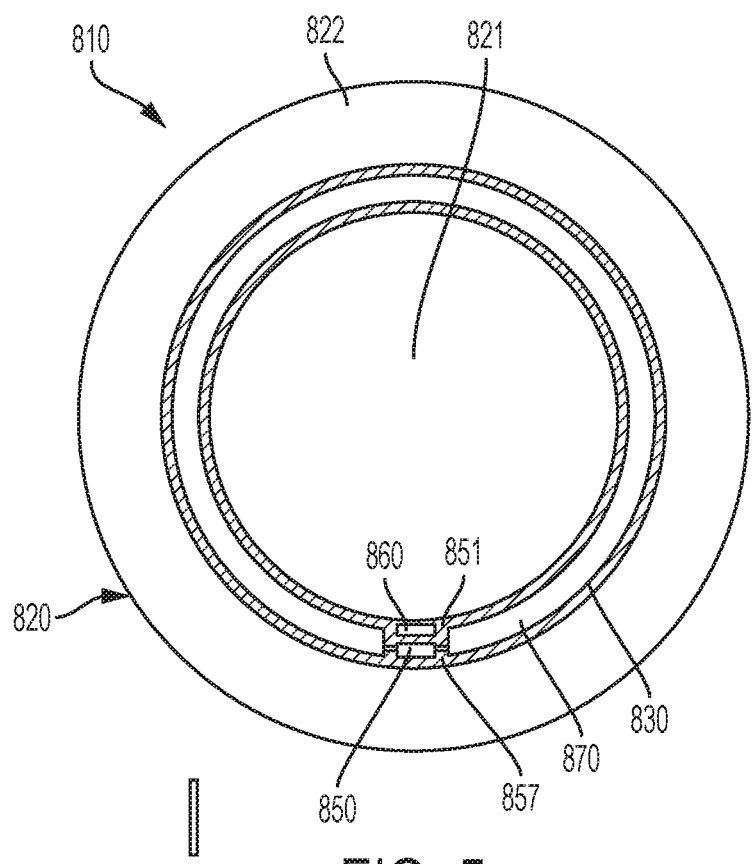
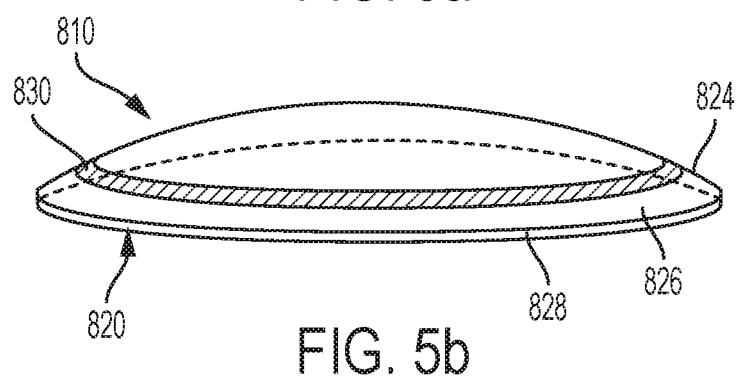

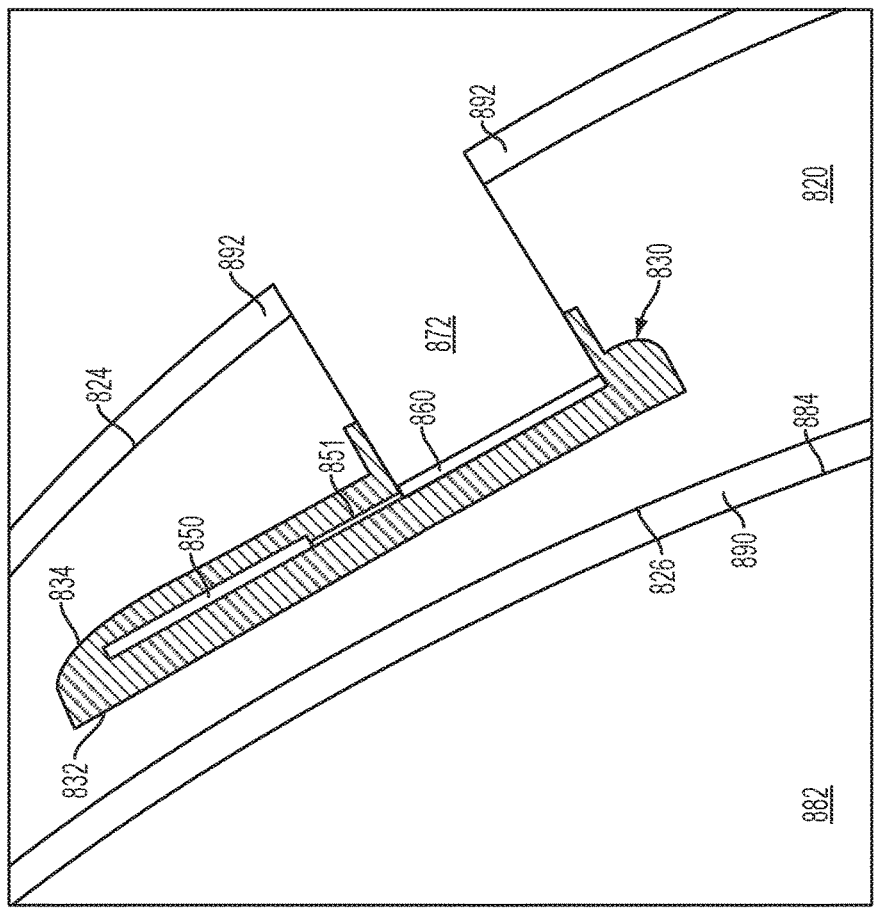
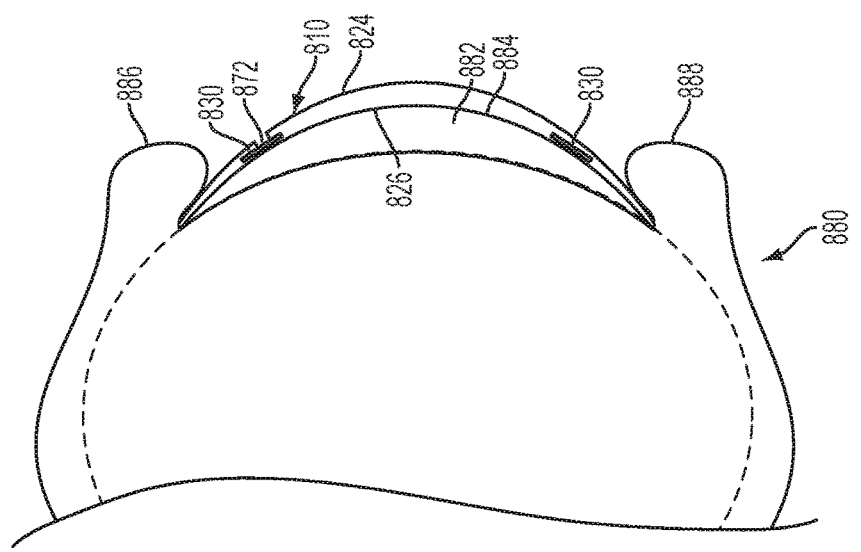
FIG. 5d
FIG. 5c

BODY-MOUNTABLE DEVICES HAVING AN OPTICAL POLARIZER

CROSS-REFERENCE TO RELATED APPLICATIONS

This application is a continuation of U.S. patent application Ser. No. 14/199,440, filed Mar. 6, 2014, which is fully incorporated by reference herein for all purposes.

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, the present disclosure provides a method. The method involves: forming a first polymer layer, the first polymer layer comprising a first liquid crystal elastomer; positioning a structure on the first polymer layer; and forming a second polymer layer over the first polymer layer and the structure, the second polymer layer comprises a second liquid crystal elastomer, wherein the first polymer layer defines a first side of a body-mountable device and the second polymer layer defines a second side of the body-mountable device opposite the first side, and wherein the application of an electric field across the first polymer layer and the second polymer layer causes the body-mountable device to polarize or depolarize in response to the electric field.

In another aspect, the present disclosure provides a body-mountable device. The body-mountable device involves: a first polymer layer, the first polymer layer comprising a first liquid crystal elastomer; a structure on the first polymer layer, the structure comprising sensor; and a second polymer layer over the first polymer layer and the structure, the second polymer layer comprises a second liquid crystal elastomer, wherein the first polymer layer defines a first side of a body-mountable device and the second polymer layer defines a second side of the body-mountable device opposite the first side, and wherein the application of an electric field across the first polymer layer and the second polymer layer causes the body-mountable device to polarize or depolarize in response to the electric field.

In another aspect, a method is provided. The method involves: forming a first polymer layer, the first polymer layer comprising a first liquid crystal elastomer; forming a second polymer layer over the first polymer layer, the second polymer layer comprising a second liquid crystal elastomer, wherein the first polymer layer, the second polymer layer, or both are formed by the polymerization of a liquid crystal pre-polymer in the presence of an electric or magnetic field, and wherein the application of an electric field across the first polymer layer and the second polymer layer causes the body-mountable device to polarize or depolarize in response to the electric field.

In another aspect, a contact lens is provided. The contact lens involves: a first polymer layer, the first polymer layer comprising a first liquid crystal elastomer; and a second polymer layer, the second polymer layer comprising a second liquid crystal elastomer, wherein the first polymer layer, the second polymer layer, or both are formed by polymerization of a liquid crystal pre-polymer in the presence of an electric or magnetic field, and wherein the application of an electric field across the first polymer layer and the second polymer layer causes the contact lens to polarize or depolarize in response to the electric field.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5a is a top view of an eye-mountable device, according to an example embodiment.

FIG. 5b is a side view of an eye-mountable device, according to an example embodiment.

FIG. 5c is a side cross-section view of the eye-mountable device of FIGS. 5a and 5b while mounted to a corneal surface of an eye, according to an example embodiment.

FIG. 5d is a side cross-section view showing the tear film layers surrounding the surfaces of the eye-mountable device mounted as shown in FIG. 5c, according to an example embodiment.

DETAILED DESCRIPTION

Figure 1A:
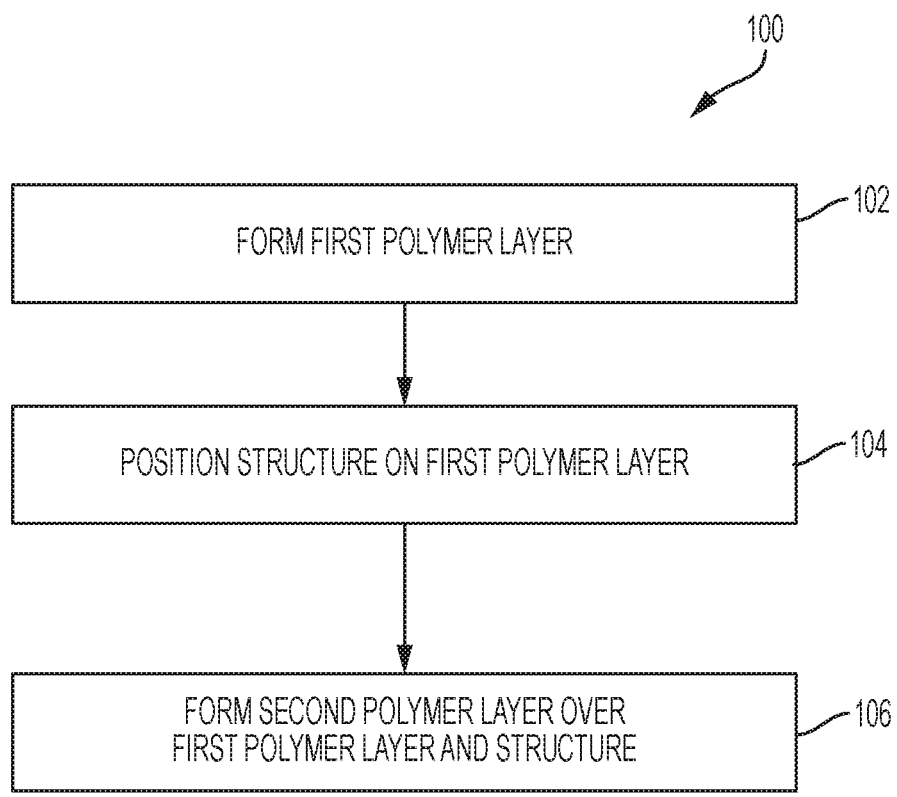
FIG. 1a is a flow chart illustrating a method according to an example embodiment, without the use of an electric or magnetic field during curing of the first and second polymer layers.

The following detailed description describes various features and functions of the disclosed methods, apparatus, and systems with reference to the accompanying figures. In the figures, similar symbols typically identify similar components, unless context dictates otherwise. The illustrative method, apparatus, and system embodiments described herein are not meant to be limiting. It will be readily understood that certain aspects of the disclosed methods, apparatus, and systems can be arranged and combined in a wide variety of different configurations, all of which are contemplated herein.

I. Introduction

Polarized lenses are widely used for reducing glare by incorporating a filter that blocks the passage of light that is horizontally polarized from surfaces. However, polarized lenses are problematic to users attempting to view electronic displays based on liquid crystal materials which typically emit plane polarized light. As a result, users are unable to clearly view images liquid crystal displays and are forced into a repetitive cycle of removing/repositioning their polarized glasses in order to improve visibility of displays and colors. Beneficially, the embodiments described herein may improve visibility and allow for monitoring of health-related information.

A body-mountable device in the form of contact lenses may be configured to monitor health-related information based on at least one analyte detected in a fluid of a user wearing the body-mountable device and reduce glare. Such a body-mountable device may include a structure located between a first polymer layer comprising a first liquid crystal elastomer and second polymer layer comprising a second liquid crystal elastomer. Further, the structure may include one or more components, such as a sensor that is configured to detect at least one analyte. Each of the first and second liquid crystal elastomers includes a polymer scaffold on to which mesogens are covalently attached which can be oriented by the application of an electric field and in turn changes the polarization state of each layer. Thus, when an electric field is applied across the first and second polymer layers of the device, each layer separately either polarizes or depolarizes in response to the electric field, changing the amount and orientation of light reaching the eye. A signal may be sent wirelessly by the user or via a sensor on a pair of glasses or in the body-mountable device to apply an electrical current across electrodes and cause the first and second polymer layers to polarize or depolarize at will or as needed and to allow users to control glare and improve visibility of electric liquid crystal displays.

As used throughout this disclosure, the anterior side of the body-mountable device refers to an outward-facing side of the body-mountable device, whereas the posterior side of the body-mountable device refers to an inward-facing side of the body-mountable device. In particular, when the body-mountable device comprises an eye-mountable device and the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Methods

Example methods for forming a body-mountable device are disclosed. FIG. 1a is a flow chart illustrating a method 100 according to an example embodiment. More specifically, as shown by block 102, the method 100 may involve forming a first polymer layer 308. Further, as shown by block 104, the method 100 may involve positioning, by any suitable means, a structure on the first polymer layer 308, wherein the structure comprises a sensor. Further still, as shown by block 106, the method 100 may involve forming a second polymer layer over the first polymer layer 308 and the structure, wherein the first polymer layer 308 defines a first side of the body-mountable device and the second polymer layer defines a second side of the body-mountable device opposite the first side.

For purposes of illustration, the method 100 is described below as being carried out by a fabrication device that utilizes various methods and/or processes for fabricating body-mountable devices. It should be understood, however, that the method 100 may be carried out by a fabrication device that utilizes other methods and/or processes for fabricating body-mountable devices.

Moreover, for purposes of illustration, the method 100 is described below in a scenario where a body-mountable device comprises an eye-mountable device. It should be understood, however, that the method 100 may involve scenarios where the body-mountable device comprises other mountable devices that are mounted on or in other portions of the human body. For example, the body-mountable device may comprise a tooth-mountable device and/or a skin-mountable device.

Method 100 will now be described in greater detail below with reference to FIGS. 2a-2d. It is noted that relative dimensions in FIGS. 2a-2d are not necessarily to scale, but have been rendered for purposes of explanation only in describing method 100.

A. Forming a First Polymer Layer

Figure 2A:
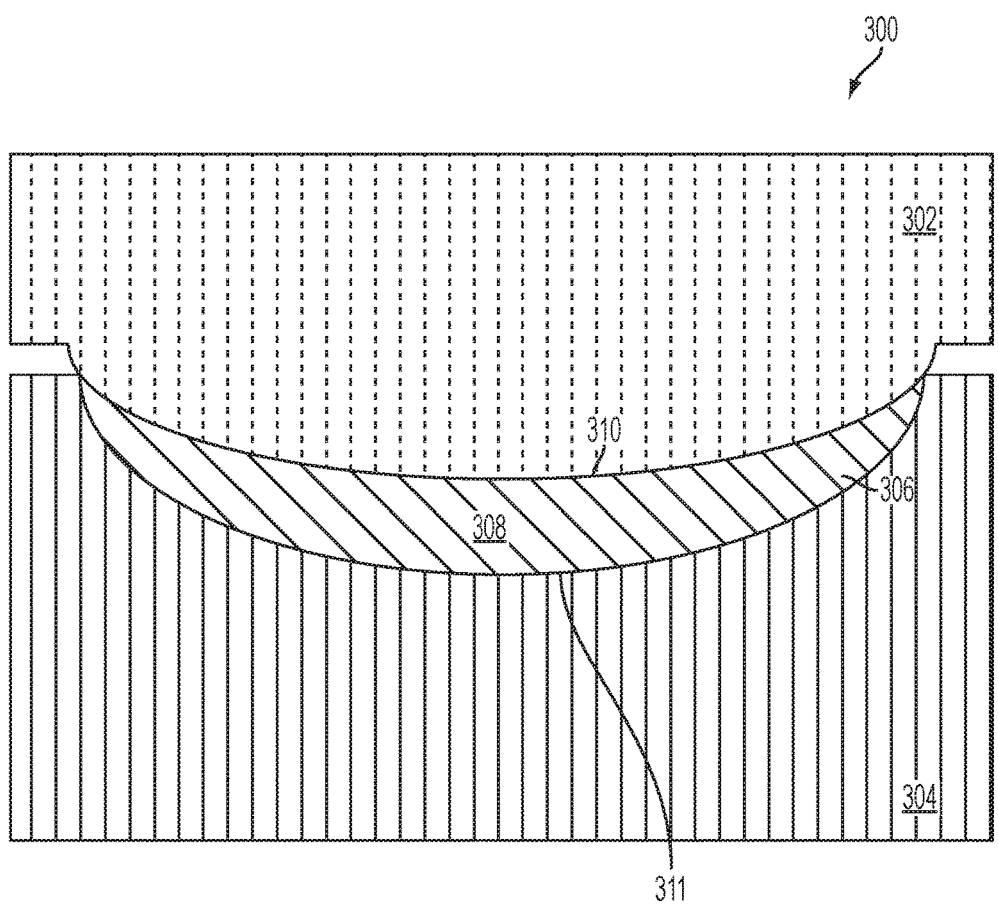
FIG. 2a is an illustration of formation of a first polymer layer, according to an example embodiment.

As mentioned above, at block 102, the fabrication device may be used to form a first polymer layer 308. The fabrication device may include molding pieces, such as molding pieces that are suitable for cast molding. FIG. 2a illustrates a fabrication device 300 that includes molding pieces that may be used to form the first polymer layer 308. In particular, FIG. 2a illustrates the fabrication device 300 including a first molding piece 302 and a second molding piece 304. The first molding piece 302 and the second molding piece 304 may define a first cavity. A polymer material 306 may be provided on a surface of the second molding piece 304, and the polymer material 306 may be compressed into a first polymer layer 308 by the first molding piece 302. In an example, the polymer material 306 may be provided on the surface of the second molding piece 304 by filling the second molding piece 304 with the polymer material 306.

After the polymer material 306 is compressed into the first polymer layer 308, the fabrication device 300 may cure the first polymer layer 308. In an example, the polymer material 306 can be a heat or UV-curable polymer material, and the fabrication device 300 may be configured to cure the heat or UV-curable polymer material using heat or UV light. In an example, the first polymer layer 308 may be cured to a partially-cured state. In such an example, this may involve curing the material to a partially-cured state that is approximately 50-75% of a fully cured state. Other partially-cured states are possible as well. Beneficially, by partially curing the first polymer layer 308 to a partially-cured state, the first polymer layer 308 may have a tackiness that facilitates adhesion thereto. With this arrangement, the tackiness may facilitate a structure placed on the first polymer layer 308 remaining securely fixed in a given location during subsequent formation steps.

The tackiness exhibited by the partially-cured first polymer layer 308 may be different for different polymers. Accordingly, the fabrication device 300 may be configured to cure different polymer materials differently than other polymer materials (e.g., a first polymer material may be cured more than a second polymer material). Further, in addition to light curing, other methods of curing are possible as well, such as chemical additives and/or heat. For instance, the first polymer material may be cured at a certain temperature, such as between 100 degrees Celsius (C) to 150 degrees C. Yet still further, in other example embodiments, the first polymer layer 308 may be completely cured. Alternatively, the fabrication device 300 may bypass curing the first polymer layer 308 at this stage.

The first molding piece 302 and the second molding piece 304 may be configured to achieve a given desired thickness of the first polymer layer 308. For instance, in an example, the first polymer layer 308 can have a thickness of less than 150 micrometers. In an example embodiment, the first molding piece 302 and the second molding piece 304 can be designed so as to allow for a layer having less than a 150 micrometer thickness between the two cavities. As such, when the first molding piece 302 and the second molding piece 304 are pressed together during the formation of the first polymer layer 308, the resulting polymer layer 308 will have a thickness of less than 150 micrometers.

In an example, the thickness of the first polymer layer 308 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 306 can be any liquid crystal material that can form an eye-compatible polymer layer. For example, the polymer material 306 may be a formulation or pre-polymer mixture containing polymerizable monomers to form a bio-compatible liquid crystal elastomer. Further, the polymer material 306 may form a transparent or substantially transparent polymer layer. As such, the use of the polymer material 306 may result in an eye-mountable device through which the wearer can see when mounted on the wearer's eye.

The term "bio-compatible" or "bio-compatibility," as used in this disclosure, refers generally to the ability of a material or device to co-exist with a biological host. Bio-compatible materials are generally those that do not bring about a host response (such as an immune response) that results in deleterious effects to either the biological host or the material. In addition to being bio-compatible, the first polymer layer 308 may be an electrically insulating material to isolate encapsulated structure 314 from the surrounding environment.

Liquid crystal elastomers are a hybrid material that combines liquid crystal orientational order with the elastic properties of a polymer network component into a single composite material. Liquid crystal elastomers are rubbery networks composed of long, cross-linked polymer chains that may also display liquid crystalline behavior, including ordering into nematic, cholesteric or smetic phases. The rubber elasticity is a unique feature of polymer networks or elastomers formed from long polymer chains connected to one another by cross-linkages. The implanting or grafting of rod-like or disk-like mesogenic monomer units into the network chains can induce the liquid crystalline state of the elastomers.

Liquid crystalline molecules consist of a rigid moiety and one or more flexible parts. The rigid part, referred to as the mesogen, plays a role in molecular alignment whereas the flexible parts induce fluidity. Liquid crystal elastomers exhibit a remarkable stimulus-deformation response to external stimuli such as heat, light irradiation, magnetic fields, and/or electric fields. In the presence of such stimuli, liquid crystal elastomers undergo a spontaneous and reversible shape change as it moves from a passive, unstimulated state to an active, stimulated state.

For liquid crystal elastomers that can be oriented by electrical fields, liquid crystal elastomers possessing a mesogen having a strong dipole moment work can be desirable. A large variety of liquid crystal elastomers incorporating different mesogens and cross-linking chemistries have been synthesized and reported, using a variety of synthetic pathways. Their preparation generally involves covalently linking a minimum of three components: (a) polymer component; (b) liquid crystal mesogen component; and (c) cross-linker component. The most commonly used methods for synthesizing liquid crystal elastomers include the siloxane-vinyl hydrosilylation reaction (Finkelmann reaction) or acrylate polymerization reaction of acrylate functionalized LC mesogens and cross-linkers. See, for instance, Ohm et al., *Adv. Mater.*, 2010, vol. 22, pp. 3366-3387) and K. Urayama, *Macromolecules*, 2007, vol. 40 (7), pp. 2277-2288 which provide an overview of liquid crystal elastomers and provides examples of suitable liquid crystal elastomers.

In one embodiment, the first polymer layer 308 comprises a liquid crystal elastomer. Any suitable liquid crystal elastomers may be used to prepare the first polymer layer 308, particularly electrically active liquid crystal elastomers that may be oriented by the application of an electrical field, including ferroelectric liquid crystal elastomers and liquid crystal elastomers having mesogens with a relative strong dipole moment. Representative examples of suitable electrically active liquid crystal elastomers include, without limitation, vinylsiloxane monomers co-polymerized with different crosslinkers (e.g., trivinyl-terminated-1,3,5-trihydroxylphenyl groups, dimethylsiloxane, polyethylene glycol, etc.) and mesogenic biphenyl, cyanobiphenyl (e.g. 4-cyano-4'-pentylbiphenyl (5CB)), azobenzene, diazobenzene, bipyridinyl, and substituted phenylbenzoate esters (e.g., 4'-cyanophenyl 4-heptylbenzoate (7CPB)). The second polymer layer 376, as discussed below, comprises a second liquid crystal elastomer which may be the same or different from the first liquid crystal elastomers.

A mixture of a polymerizable pre-polymer mixture that will form the first polymer layer 308 is layered onto the substrate and polymerized to form the first polymer layer 308. Polymerization may be initiated by any suitable means including heat or UV rays. The pre-polymer mixture may be prepared before applying it to the substrate or may be mixed in situ on the substrate. Moreover, the first polymer layer 308 may have a variety of thicknesses. For example, the first polymer layer 308 may have a thickness of between 5 to 50 micrometers, such as 15 micrometers. Other thicknesses of the first polymer layer 308 are possible as well.

Figure 1B:
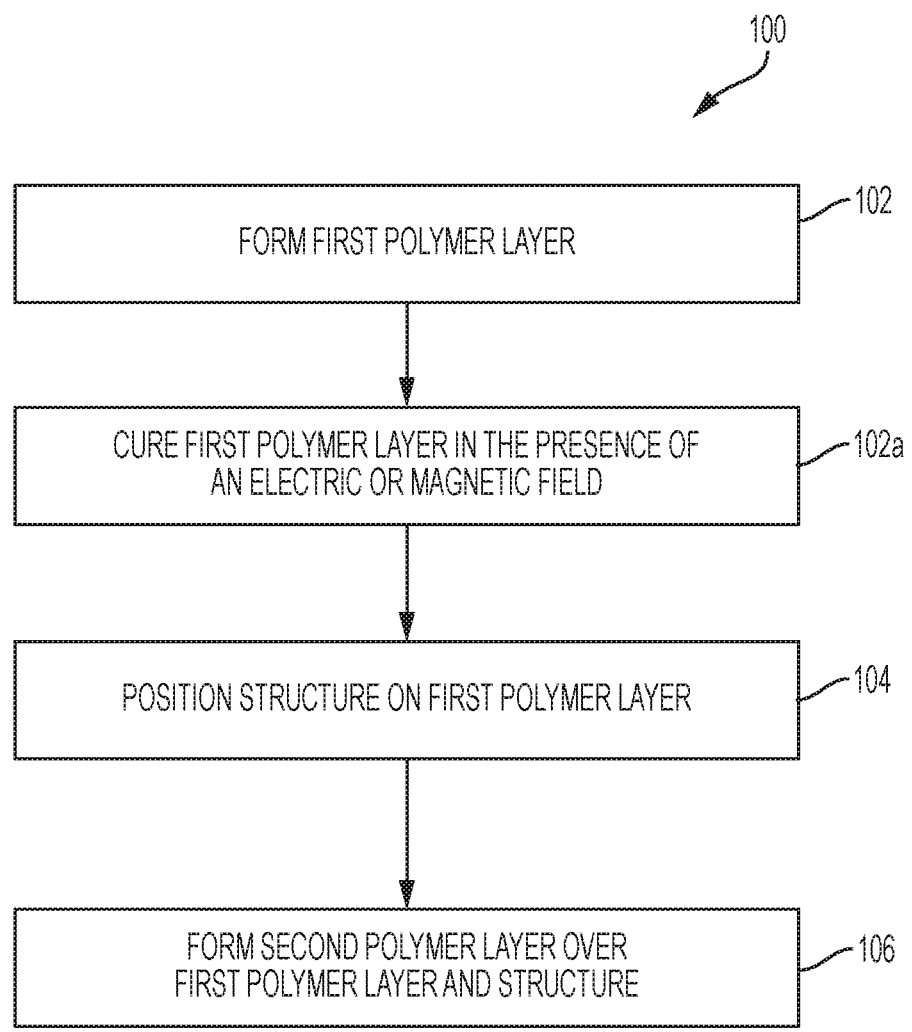
FIG. 1b is a flow chart illustrating a method according to an example embodiment, with the use of an electric or magnetic field during curing of the first polymer layer.

Electric or magnetic fields applied during polymerization or curing of the first polymer layer 308, shown as block 102*a* in FIG. 1*b*, can affect the orientation of the mesogens such that they will align along the field direction or far field director of the applied field and result in the first polymer layer 308 having a nematic orientation in its passive, unstimulated state, If an electric or magnetic field is absent during the polymerization step, the resulting first polymer layer 308 after polymerization will have a isotropic or random orientation at its passive, unstimulated state.

In one aspect, the pre-polymer mixture forming the first liquid crystal elastomers may be layered onto the substrate between a plurality of electrodes which may generate an electric or magnetic field of any suitable strength while the first liquid crystal elastomers is curing or polymerizing to produce a first polymer layer 308 that is nematically oriented in its passive, inactive state.

The applied electric field may be generated between electrodes that are positioned in any suitable matter on the body-mountable device so as to sandwich the first polymer layer 308. For example, the electrodes may be positioned on the inner surfaces of the molding cavity defined by the first molding piece 302 and a second molding piece 304 shown in FIG. 1. Alternatively, the electrodes may be positioned on the inner surface of the second molding piece 304 and structure 314 shown in FIG. 2c. The electrodes may also provide a mechanism for active switching of the alignment of the mesogens of the liquid crystal elastomers in the body-mountable device, thus controlling the orientation and polarization of light that passes through the lens to the eye.

Any suitable electrodes may be used including transparent electrodes comprised of transparent conducting oxide such as indium oxide, tin oxide, or indium tin oxide (ITO).

In an example, the first molding piece 302 and/or the second molding piece 304 can be configured so as to allow sufficient pinch off to provide for suitable edges for an eye-mountable device.

Further, in an example, the first molding piece 302 and the second molding piece 304 may be transparent, such that the polymer material 306 may be visible during formation of the first polymer layer 308. Such an arrangement may assist in orienting the first molding piece 302 and/or the second molding piece 304.

The first polymer layer 308 defines a posterior side (or a first side) 310 of an eye-mountable device. That is, the first polymer layer 308 defines an outer edge of the eye-mountable device. When mounted on an eye of a user, the posterior side 310 of the eye-mountable device defined by the first polymer layer 308 corresponds to a side of the device touching the eye of the user. The first molding piece 302 may be shaped so as to define a shape of the posterior side 310. For example, a curvature of the posterior side 310 may be defined by the first molding piece 302. The first polymer layer 308 may also have a side 311 opposite the posterior side 310. The second molding piece 304 may be shaped so as to define a shape of the side 311. For example, a curvature of the side 311 may be defined by the second molding piece 304.

As mentioned above, although FIG. 2a illustrates forming the first polymer layer 308 through cast molding, other methods for forming the first polymer layer 308 are possible as well. For example, the first polymer layer 308 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 308 may be formed via spin casting. Through spin-casting techniques, the fabrication device 300 may form a first polymer layer 308 of a precise thickness. In an example, a spin-casting mold may be spun along its central access at a set speed, and the polymer may be introduced to the mold as the mold is spinning in order to form a first polymer layer 308. The final thickness of the first polymer layer 308 may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer 308 of a well-defined thickness.

B. Positioning a Structure on the First Polymer Layer

Figure 2B:
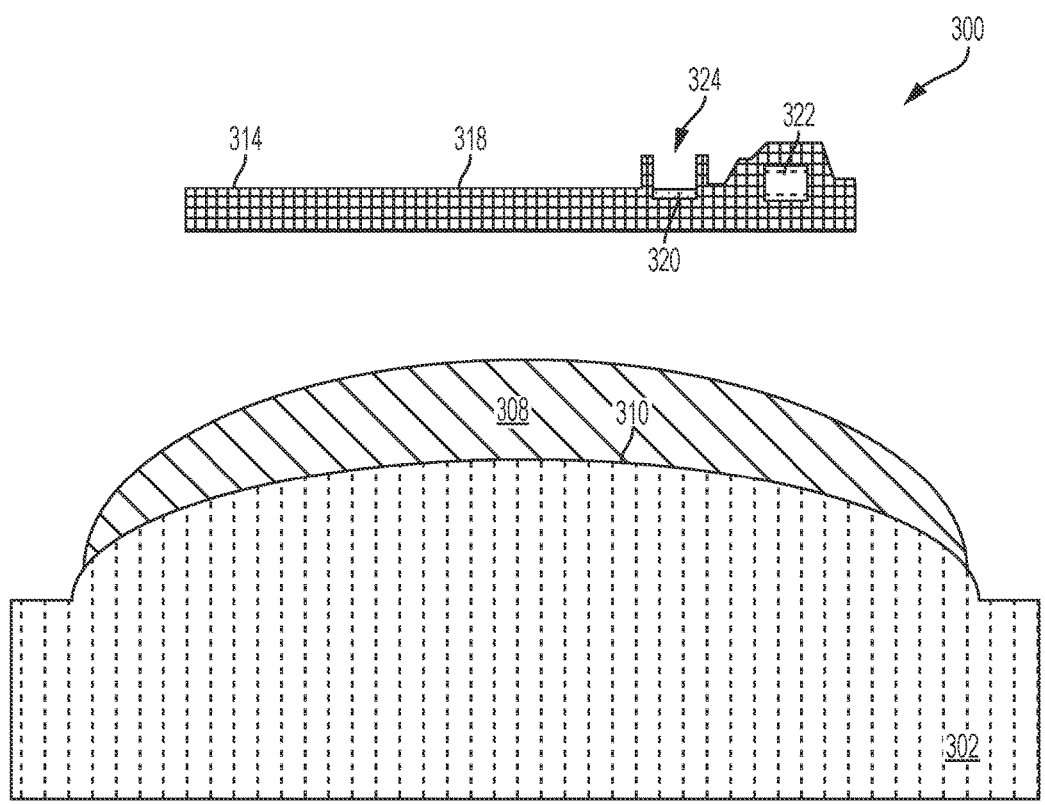
FIG. 2b is an illustration of positioning a structure on a first polymer layer, according to an example embodiment.
Figure 2C:
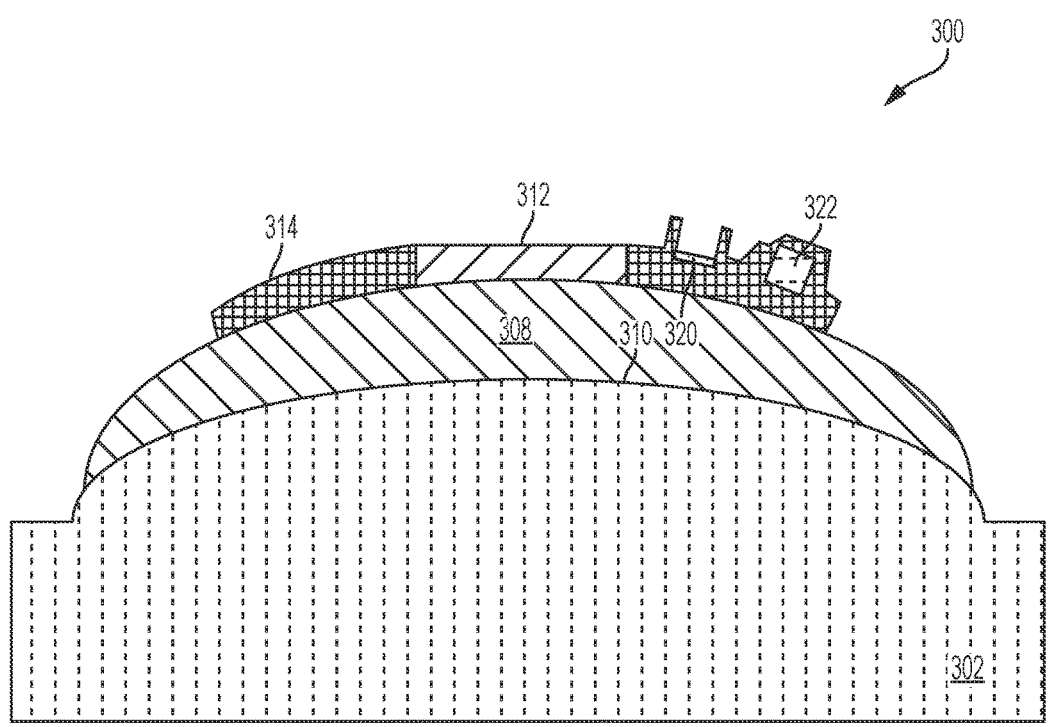
FIG. 2c is an illustration of a structure positioned on a first polymer layer, according to an example embodiment.

As mentioned above, at block 104, a structure may be positioned on the first polymer layer 308. FIGS. 2b and 2c illustrate an example in which a structure 314 is positioned on the first polymer layer 308.

In an example, the structure 314 has an outer diameter and a hole 316 that defines an inner diameter. And the structure 314 includes a polymer 318, a sensor 320, and electronics 322. The structure 314 may occupy a peripheral portion of an eye-mountable device, such as an eye-mountable device 400 illustrated in FIG. 3, so as to limit interference with a user's field of view when the eye-mountable device is mounted on an eye of the user. The polymer 318 may comprise a variety of polymeric materials, such as paralyene.

In the illustrated example, the electronics 322 is embedded in the polymer 318, and the sensor 320 is surrounded by the polymer 318, except for the sensor 320 being exposed by an opening 324. However, in other examples, the sensor 320 and electronics 322 may be mounted on a surface of the polymer 318, such as a top surface of the polymer 318. With this arrangement, the structure 314 might not include the opening 324. In some embodiments, the opening 324 can have a dimension of between 500 to 700 micrometers. Other dimensions are possible as well. And, in some embodiments, the opening 324 can have a square shape with rounded corners. Other shapes are possible as well, such as rectangular, circular, etc.

The structure 314 can have various sizes. For instance, the size of the structure 314 may depend on which analyte (or analytes) an eye-mountable device is configured to detect. In an example, the structure 314 is a substrate shaped as a ring with an outer diameter of approximately a 1 centimeter, a radial thickness of approximately 1 millimeter, and a maximum height of approximately 50 between 150 micrometers. Of course, other sizes of the structure 314 are possible as well.

In an example, the structure 314 has a height dimension of at least 50 micrometers. In other words, at some point of the structure 314, the height of the structure 314 may be at least 50 micrometers. In such an example, this height dimension may correspond to a maximum height of the structure 314. In accordance with this disclosure, the maximum height of the structure 314 corresponds to the height of the structure 314 at its highest point. For instance, in the example where the structure 314 includes the sensor 320 and the electronics 322, the height of the structure 314 may vary (and thus the structure 314 may have various height dimensions). For example, the height of the structure 314 may be higher at a point where the electronics 320 is mounted on the structure 314, whereas the height may be lower at a point where the electronics 320 is not mounted on the structure 322. In such an example, the maximum height may correspond to the point where the electronics 322 is located on the structure 314. Further, in an example, the structure 314 can be more rigid than the first polymer layer 308.

The sensor 320 can be configured in a variety of ways. As one example, the sensor 320 may comprise a pair of electrodes, such as a working electrode and a reference electrode, configured to detect one or more analytes. Other configurations of the sensor 320 are possible as well. And the sensor 320 can have a variety of thicknesses. As one example, the sensor 320 can have a thickness of 260 nanometers. Other thicknesses of the sensor 320 are possible as well.

The electronics 322 can be configured in a variety of ways. As one example, the electronics 322 can comprise a chip including one or more logic elements configured to operate the sensor 320. Other configurations of the electronics 322 are possible as well.

In order to position the structure 314, the fabrication device 300 may separate the first molding piece 302 from the second molding piece 304. When the fabrication device 300 separates the first molding piece 302 from the second molding piece 304, the first polymer layer 308 may stick to a side of the first molding piece 302. In an example, the first polymer layer 308 and/or the first molding piece 302 can be surface treated, such that the first polymer layer 308 sticks to the side of the first molding piece 302. Additionally or alternatively, the second molding piece 304 can be surface treated, such that the first polymer layer 308 sticks to the side of the first molding piece 302.

In an example, positioning the structure 314 on the first polymer layer 308 can include aligning the structure 314 with the alignment feature 312. In one example, the hole 316 in the structure 314 has an asymmetric inner diameter and the alignment feature 312 includes an asymmetric peg such that the hole 316 receives the alignment feature 312 in only a predetermined rotational orientation. However, other ways of providing a predetermined rotational orientation of the structure 314 by alignment with the alignment feature 312 are also possible.

Alternatively, the fabrication device 300 can include a positioning apparatus (not shown), such as a robotic system, configured to position the structure 314 on the first polymer layer 308 in a predetermined rotational orientation. For instance, the positioning apparatus may (i) pick up the structure 314 (e.g., via suction), (ii) position the structure 314 above the first polymer layer 308, and then (iii) lower the structure 314 toward the first polymer layer 308. When the structure 314 is positioned in a predetermined rotational orientation, the positioning apparatus may then release the structure 314 (e.g., by releasing the suction). With this approach, the first polymer layer 308 might not include the alignment feature 312.

In some embodiments, the positioning apparatus may bend the structure 314. The positioning apparatus may bend the structure 314 by applying a force and/or a torque to one or more portions of the structure 314.

The positioning apparatus may further include a vision system configured to assist with positioning the structure 314 on the first polymer layer 308. Such a vision system may facilitate guiding the structure 314 to a precise location on the first polymer layer 308. In an example, the vision system can be appropriate for situations in which one or more production specifications for an eye-mountable device, such the eye-mountable device 400, have requirements with very low tolerances related to the positioning of a sensor, such as the sensor 320, within the eye-mountable device.

During formation of an eye-mountable device, such as the eye-mountable device 400, it may be desirable for the structure 314 to remain in a fixed position during formation of the eye-mountable device. For instance, movement of the structure 314 during subsequent formation steps, such as formation of a second polymer layer 376, may result in improper placement of the structure 314 relative to the surrounding polymer layers. As one example, movement of the structure 314 during providing a molding piece with a polymer material to form the second polymer layer 376 and/or curing the second polymer layer 376 can result in improper placement of the structure 314 relative to the surrounding polymer layers.

Therefore, in an example, an adhesive is applied to the structure 314 and/or the first polymer layer 308 before the structure 314 is placed on the first polymer layer 308. The applied adhesive may facilitate adhesion of the structure 314 to the first polymer layer 308. For instance, a small amount of adhesive may be applied to a cured first polymer layer 308, and the structure 314 may be positioned on the small amount of adhesive such that the structure 314 adheres to the first polymer layer 308. Additionally or alternatively, a small amount of adhesive may be applied to the structure 314, and the structure 314 may then be placed on the first polymer layer 308 (e.g., a cured first polymer layer 308) such that the structure 314 adheres to the first polymer layer 308. With this arrangement, the structure 314 may remain adhered to the first polymer layer 308 in a secure location during subsequent formation steps.

As noted above, in an example, the first polymer layer 308 in a partially-cured state may have a tackiness that facilitates adhesion thereto. With this arrangement, the structure 314 may remain adhered to the first polymer layer 308 in a secure location during subsequent formation steps.

In some situations, such as for large-scale production purposes, it may be desirable to not only place the structure 314 in a predetermined rotational orientation, but it may also be desirable to repeatedly place and maintain the structure 314 at this precise location for a plurality of eye-mountable devices. Beneficially, formation of an eye-mountable device in accordance with an example embodiment allows for such repeatable and precise positioning.

FIG. 2c illustrates the structure 314 positioned on the first polymer layer 308. With this arrangement, the sensor 320 may be mounted at a particular angle along a circumference of the first polymer layer 308. As a result, the sensor 308 may be placed at a precise location in an XYZ plane on the first polymer layer 308. As one example, the sensor 320 may rest at a 6 o'clock position of the first polymer layer 320. As another example, the sensor 320 may rest at a 12 o'clock position of the first polymer layer 308.

Figure 2D:
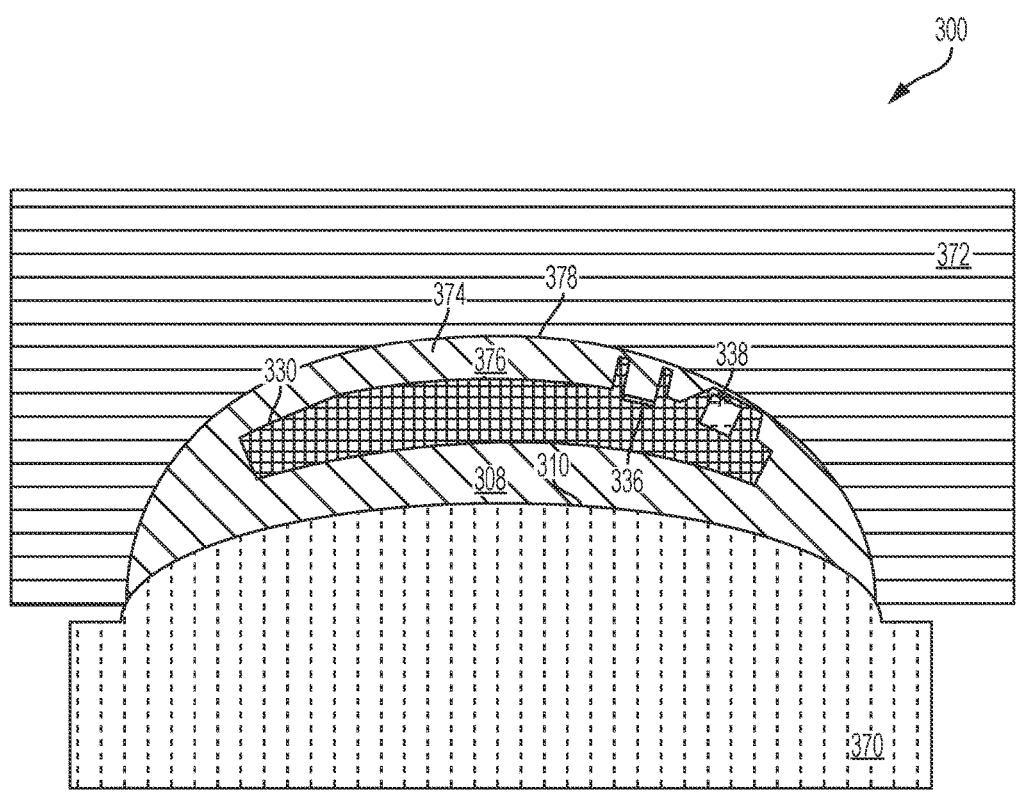
FIG. 2d is an illustration of formation of a second polymer layer, according to an example embodiment.

C. Forming a Second Polymer Layer Over the First Polymer Layer and the Structure As mentioned above, at block 106, the fabrication device may form a second polymer layer over the first polymer layer 308 and the structure, such that the structure is fully enclosed by the first polymer layer 308 and the second polymer layer 376. FIG. 2d illustrates the fabrication device 300 including example molding pieces that may be used to form the second polymer layer 376. In particular, FIG. 2d illustrates a third molding piece 370 and a fourth molding piece 372. The third molding piece 370 and the fourth molding piece 372 may define a second cavity. In some examples, the first molding piece 302 may be used as the third molding piece 370.

After the partially-fabricated device 368 is placed on the third molding piece 370, the third molding piece 370 may be filled with a polymer material 374. The polymer material 374 may be formed into a second polymer layer 376 by compression between the third molding piece 370 and the fourth molding piece 372. As a result, the second polymer layer 376 may mold over the structure 330, such that the structure 330 is fully enclosed by the first polymer layer 308 and the second polymer layer 376.

After the second polymer layer 376 is formed, the fabrication device 300 may cure the second polymer layer 376. In an example, the second polymer layer 376 can be cured like the first polymer layer 308. However, in other examples, the second polymer layer 376 may be cured by different techniques than the first polymer layer 308. The second polymer layer 376 can be cured by any of the techniques mentioned herein. In an example, the fabrication device 300 may cure the first polymer layer 308 at this stage.

Figure 3:
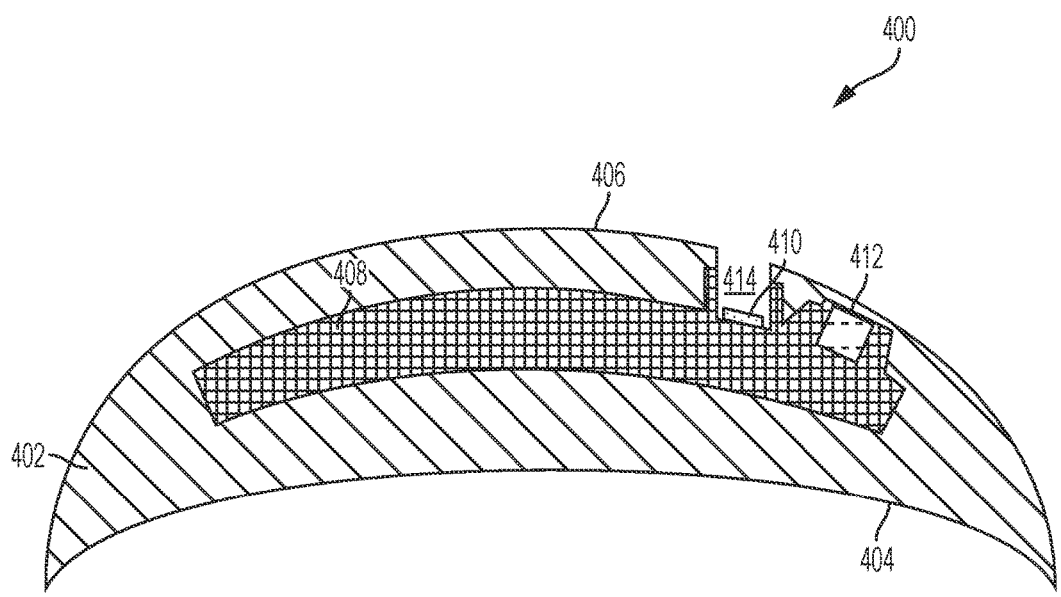
FIG. 3 is an illustration of an eye-mountable device fabricated according to an example embodiment.

After the second polymer layer 376 is cured, there may not be a visible boundary line separating the first polymer layer 308 from the second polymer layer 376. For example, FIG. 3 illustrates the fabricated eye-mountable device 400. In particular, FIG. 3 illustrates the eye-mountable device 400 includes a transparent polymer 402. The transparent polymer 402 can be arranged like the first polymer layer 308 and the second polymer layer 376.

The second polymer layer 376 may be comprised of the same liquid crystal elastomers or different liquid crystal elastomers as the first polymer layer 308. However, the second polymer layer 376 may be comprised a different liquid crystal elastomers than the first polymer layer 308.

A mixture of polymerizable pre-polymer forming the second liquid crystal elastomer may be layered onto the first polymer layer 308 and the structure 314 and polymerized to form the second polymer layer 376. The pre-polymer mixture may be pre-mixed before applying it to the first polymer layer 308 and the structure 314 or may be prepared in situ on the first polymer layer 308 and structure 314. The polymerization may be initiated by any suitable manner including heat and UV rays. Any suitable thickness of the second polymer layer 376 may be generated on the substrate. For example, the second polymer layer 376 may have a thickness between one or more embedded components and a surface of the second polymer layer 376 between 5 to 100 micrometers, such as 15 micrometers. Other thicknesses for the second polymer layer 376 are possible as well.

Figure 1C:
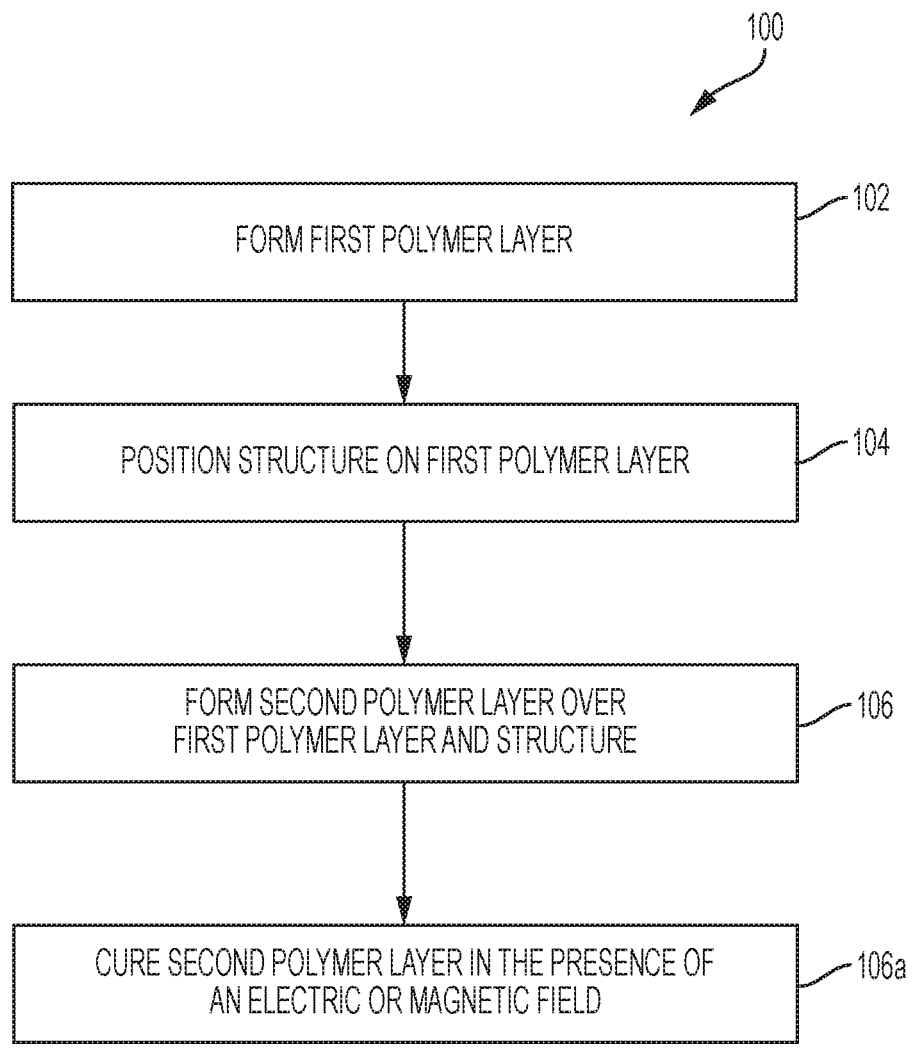
FIG. 1c is a flow chart illustrating a method according to an example embodiment, with the use of an electric or magnetic field during curing of the second polymer layer.
Figure 1D:
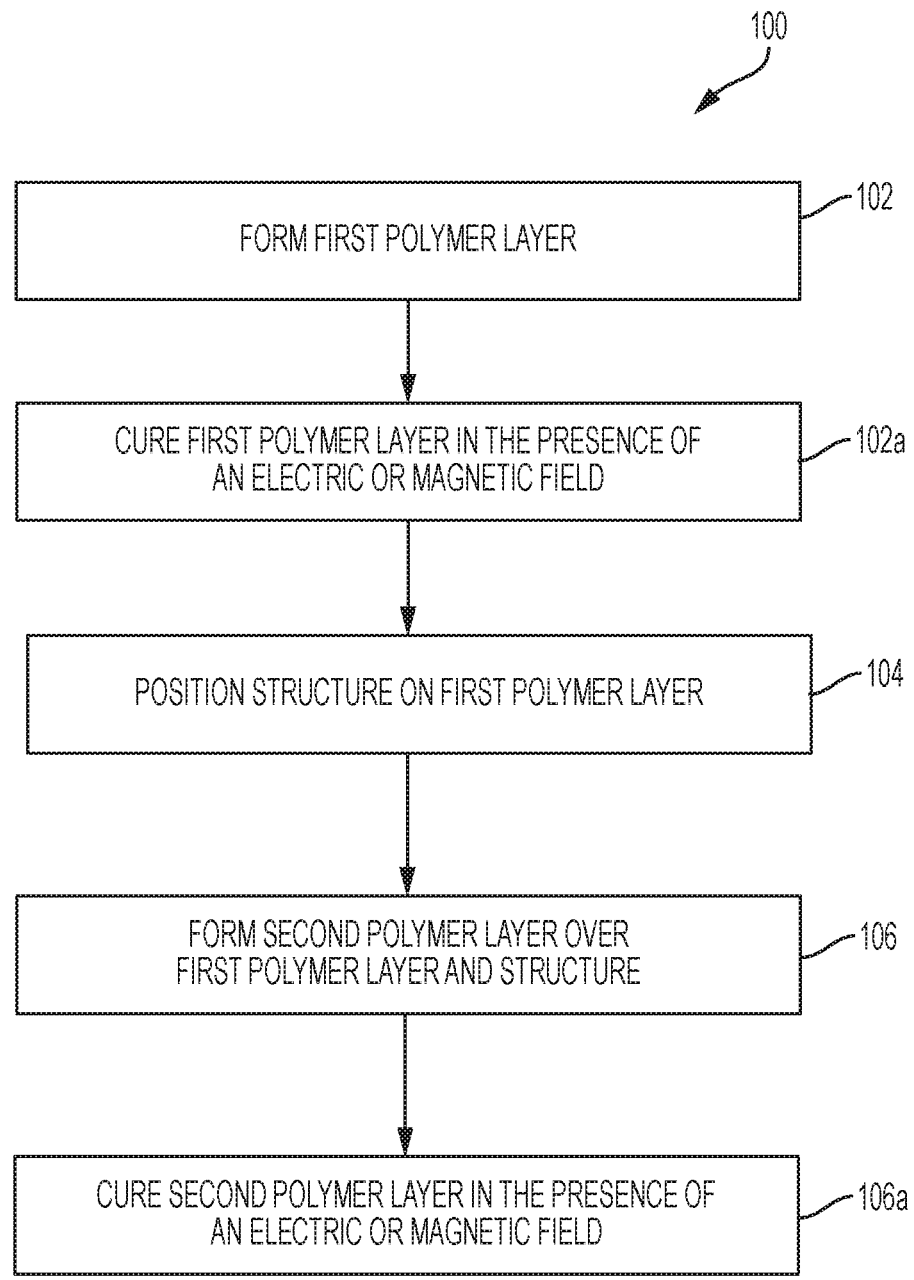
FIG. 1d is a flow chart illustrating a method according to an example embodiment, with the use of an electric or magnetic field during curing of the first and second polymer layers.

Electric or magnetic fields applied during polymerization or curing of the second polymer layer 376, shown as block 106a in FIG. 1c, will affect the orientation of the mesogens such that they will align along the field direction or far field director of the applied field and result in the second polymer layer 376 having a nematic orientation in its passive, unstimulated state. If an electric or magnetic field is absent during the polymerization step, the resulting second polymer layer 376 after polymerization will have an isotropic or random orientation at its unstimulated state.

In one aspect, the pre-polymer mixture that will form the second liquid crystal elastomers may be layered onto the first polymer layer 308 and the structure 314 between a plurality of electrodes which may generate an electric or magnetic field of any suitable strength while the second liquid crystal elastomers is curing or polymerizing to produce a second polymer layer 376 that is nematically oriented in its passive, inactive state.

The applied electric field may be generated between electrodes that are positioned in any suitable matter on the body-mountable device so as to sandwich the second polymer layer 376. For example, the electrodes may be positioned on the outer surfaces of the first polymer layer 308 and the second polymer layer 376 facing the inner surfaces of the molding cavity defined by the third molding piece 370 and a fourth molding piece 372 shown in FIG. 2d. Alternatively, the electrodes may be positioned on the outer surface of structure 314 facing the second polymer layer 376 and the outer surface of the second polymer layer 376 facing the inner surface of the fourth piece 372 as shown in FIG. 2d. The electrodes may also provide a mechanism for active switching the alignment of the mesogens of the liquid crystal elastomers in the body-mountable device, thus controlling the orientation and polarization of light that passes through the lens to the eye.

Any suitable electrodes may be used including transparent electrodes comprised of transparent conducting oxide such as indium oxide, tin oxide, or indium tin oxide (ITO).

Returning to FIG. 2d, the fabrication device 300 may further comprise one or more alignment pins (not shown), such as a plurality of dowel pins, for aligning the fourth molding piece 372 and the third molding piece 370. The one or more alignment pins can assist in forming the second polymer layer 376 by aligning the fourth molding piece 372 with the first molding piece 370.

The third molding piece 370 and the fourth molding piece 372 may be configured to achieve a given desired thickness of a layer formed between the two pieces. As one example, the third molding piece 370 and the fourth molding piece 372 may be designed so as to define a thickness of the second polymer layer 376. As another example, the third molding piece 370 and the fourth molding piece 372 may be designed so as to define a final thickness of an eye-mountable device, such as the eye-mountable device 400. In an example, the third molding piece 370 and the fourth molding piece 372 can be designed so as to allow for a layer having a given desired thickness between the two pieces (in addition to a thickness of the first polymer 308). As such, when the third molding piece 370 and the fourth molding piece 372 are pressed together during formation of a layer, the resulting layer will have the given desired thickness.

In an example, the second polymer layer 376 has a thickness of greater than 50 micrometers. However, in other examples, the second polymer layer 376 can have a thickness between 50 and 300 micrometers, such as 130 micrometers. It should be understood that since the second polymer layer 376 molds over the structure 330, the second polymer layer 376 may not have a uniform thickness. For instance, the thickness of the second polymer layer 376 above the sensor 336 may be less than the thickness of the second polymer layer 376 that is not touching the sensor 336.

In an example, the thickness of the second polymer layer 376 can be selected based on a particular analyte or analytes that the eye-mountable device, such as the eye-mountable device 400, is configured to detect. For example, an optimal thickness for a first analyte may be 10 micrometers, while an optimal thickness for a second analyte may be 25 micrometers. Other examples are possible as well.

In an example, the second polymer layer 376 can be composed of the same polymer material as the first polymer layer 308. However, in other examples, the second polymer layer 376 can be composed of a different polymer material than the first polymer layer 308. The second polymer layer 376 can be any one of the polymer materials mentioned herein. In an example, the structure 330 can be more rigid than the second polymer layer 376.

The second polymer layer 376 defines an anterior side 378 (or second side) of an eye-mountable device. That is, the second polymer layer 376 defines an outer edge of the eye-mountable device. When mounted on an eye of a user, the anterior side 378 of the eye-mountable device defined by the second polymer layer 376 corresponds to the side of the device that is not touching the eye of the user. The fourth molding piece 372 may be shaped so as to define a shape of the anterior side 378. For example, a curvature of the anterior side 378 may be defined by the fourth molding piece 372.

E. Forming a Channel to the Sensor

The method 100 may further involve forming a channel to the sensor 336, such that the sensor 336 is configured to receive one or more analytes via the channel. The channel could be formed in a variety of ways. As one example, the channel may be formed by removing material from the second polymer layer 376. The material from the second polymer layer 376 may be removed to form the channel in a variety of ways. For instance, the material from the second polymer layer 376 may be removed to form the channel via a process that includes drilling, ablation, etching, etc.

As another example, a mask layer may be formed over sensor 336 before forming the second polymer layer 376. With this arrangement, the second polymer layer 376 may mold over the mask layer. In some situations, the mask layer may take the shape of the opening 340. Further, in such an example, the mask layer may be removed to form the channel to the sensor 336. The mask layer may be removed in a variety of ways. For instance, the mask layer may be removed via a process that includes etching the mask layer, dissolving the mask layer in a fluid, and/or soaking the mask layer in a fluid.

As still another example, the channel may be molded. For instance, the second polymer layer 376 may be formed in a molding piece that includes a protrusion that extends from a surface of the molding piece to the sensor 336 through the second polymer layer 376 as the second polymer layer 376 is being formed. With this arrangement, the protrusion may form the channel to the sensor 336.

As mentioned above, FIG. 3 illustrates the eye-mountable device 400 formed according to an example embodiment. In the eye-mountable device 400, a structure 408 is embedded in the transparent polymer 402. In some examples, the structure 408 may be embedded in the transparent polymer 402 in a predetermined orientation, such as centered in the transparent polymer 402.

The structure 408 includes a sensor 410 configured to detect an analyte and electronics 412. The eye-mountable device 400 includes a posterior side 404 and an anterior side 406. The transparent polymer 402 may take the form of or be similar in form to the first polymer layer 308 and the second polymer layer 376, the structure 408 may take the form of or be similar in form to the structure 330, the sensor 410 may take the form of or be similar in form to the sensor 336, and the electronics 412 may take the form of or be similar in form to the electronics 338.

In an example, the sensor 314 may be configured to receive the analyte via a channel 414 in the transparent polymer 402. With this arrangement, the structure 408 is fully enclosed by the transparent polymer 402, except for the sensor 414 being exposed by the channel 414.

In some examples, one or more dimensions of the channel 414 may be based on one or more dimensions of the sensor 410 and/or the electronics 412. As one example, a width of the channel 414 can be based on a width of the sensor 410. As another example, a height of the channel 414 can be based on a height of the electronics 412.

While the body-mountable device has been described as comprising the eye-mountable device 400, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Systems and Devices

In one embodiment, a body-mountable device is an eye mountable device in the form of contact lens, whereby the intensity or polarization of light reaching the cornea may be controlled by a plurality of electrodes which generate an electric field across the first polymer layer 308 and the second polymer layer 376. The first polymer layer 308 and second polymer layer 376 are made from bio-compatible liquid crystal elastomers having mesogens with a dipole moment. If desired, either the first polymer layer 308 (as shown as block 102a in FIG. 1b), the second polymer layer 376 (shown as block 106a in FIG. 1c), or both (as shown as blocks 102a and 106a in FIG. 1d) may be prepared by polymerization of a pre-polymer material in the presence of an applied electric or magnetic field. The presence of the applied electric or magnetic field causes the mesogens of liquid crystal elastomers to orient along the far field director of the applied electric field, resulting in first polymer layer 308, second polymer layer 376, or both to have a nematic orientation. In the absence of any such applied electric or magnetic field during polymerization, the first polymer layer 308 and the second polymer layer 376 will have a random or isotropic orientation at its inactive, passive state.

When an electric field is applied to the nematically oriented first and/or second polymer layer 376 of the contact lens, the mesogens of the nematically oriented first and/or second polymer layer 376 changes it orientation such that it may become aligned with the far-field director of the applied electric field or becomes disordered (isotropic) as it moves from its passive, inactive (polarized) state into an active (non-polarized) state, thus increasing the total amount of light reaching the cornea and improving the visibility of electronic liquid crystal displays.

When an electric field is applied to the isotropically oriented first and/or second polymer layer, the mesogens of the isotropically oriented first and/or second polymer layer re-orients into a nematic orientation as it moves from its passive, inactive (non-polarized) state into an active (polarized) state, thus reducing the total amount of light reaching the cornea and reducing the amount of glare as a result.

Thus, when an electric field is applied across the first and second polymer layers of the contact lens, each polymer layer may separately polarizes or depolarizes in response to the electric field as each layer moves from a passive (inactive) state to an active state, changing the amount of light reaching the eye. A signal may be sent wirelessly by the user or via a sensor on a pair of glasses or in the body-mountable device to apply an electrical current across electrodes and generate an applied electric field which causes the first and/or second polymer layers to polarize or depolarize at will or as needed and to allow users to control glare and improve visibility of electric liquid crystal displays.

A plurality of electrodes may be positioned at any suitable position on the body-mountable device such as a contact lens such that an applied electric field may be generated across the first and second polymer layers. For instance, the electrodes may be positioned on the outside surfaces of the first polymer layer 308 and second polymer layer 376 to sandwich the first and second polymer layers. The electrodes may be positioned on the outside surface of the first polymer layer 308 and the inside of the layer 308; alternatively the electrodes may be positioned on the inside and outside surfaces of layer 376. The electrodes may also be positioned on the same surface of layer 308 (such as the outside or inside layer) at opposite edges; alternatively the electrodes may be positioned on the same surface of layer 376 (such as the outside or inside layer) at opposite edges.

In one embodiment, a contract lens is fabricated such that the top layer of the lens and the bottom layer of the lens contain liquid crystal elastomers in which one layer is isotropic and the other layer is nematic.

In one aspect, the first polymer layer 308 of the contact lens comprises a first liquid crystal elastomer prepared from a LC pre-polymer that was cured without orienting the liquid crystal mesogens with an electric or magnetic field, resulting in a first polymer layer 308 that is isotropically oriented. Once the structure 314 is placed on the first polymer layer 308 as previously described, a second polymer layer 376 comprising a second liquid crystal elastomer is prepared by layering a second liquid crystal pre-polymer on the structure 314 and the first polymer layer 308. The second polymer layer 376 has an isotropic ordering. When an electrical field is applied to the completed contact lens, the mesogens in the first and second polymer layers re-orient themselves from an passive, inactive state (isotropic) to an active state (nematic) as a result of the applied electrical field, thus changing the amount and polarization of light that can pass through the lens and reach the cornea. When the electrical field is turned off, the liquid crystal elastomers relax back to their ground state, in which the ordering is isotropic and there is no preference for the transmission of polarized light through the lens.

In another aspect, the first polymer layer 308 of the contact lens comprises a first liquid crystal elastomer prepared from a liquid crystal pre-polymer that was cured while orienting the LC mesogens with an electric or magnetic field, resulting in a first polymer layer 308 that is nematically oriented. Once the structure 314 is placed on the first polymer layer 308 as previously described, a second polymer layer 376 comprising a second liquid crystal elastomers is prepared by layering a second pre-polymer on the structure 314 and first polymer layer 308 then cured in the presence of an applied electric or magnetic field. The resulting second polymer layer 376 is nematically oriented. In their equilibrium state, the liquid crystal elastomer lenses only allow plane polarized light to be transmitted through the lens. When an electrical field is applied to the completed contact lens, the mesogens in the first and second polymer layers re-orient themselves from an passive, inactive state (nematic) to an active state (isotropic) as a result of the applied electrical field, thus increasing the amount of light that pass through the lens to the cornea. When the electrical field is turned off, the liquid crystal elastomers relax back to their ground state, in which the ordering is nematic and there is a preference for the transmission of polarized light through the lens.

In another aspect, the first polymer layer 308 of the contact lens comprises a first liquid crystal elastomer prepared from a liquid crystal pre-polymer that was cured while orienting the LC mesogens with an electric or magnetic field, resulting in a first polymer layer 308 that is nematically oriented. Once the structure 314 is placed on the first polymer layer 308 as previously described, a second polymer layer 376 comprising a second liquid crystal elastomers is prepared by layering a second pre-polymer on the structure 314 and first polymer layer 308 then cured without any applied electric or magnetic field. The resulting second polymer layer 376 is isotropically oriented. When an electrical field is applied to the completed contact lens, the mesogens in the first and second polymer layers re-orient themselves from an passive, inactive state to an active state as a result of the applied electrical field, thus changing the amount of light that can pass through the cornea. When the electrical field is removed, the liquid crystal elastomer relaxes back to its equilibrium state in which layer 308 is nematic and layer 376 is isotropic.

In another embodiment, curing the first polymer layer 308 in the absence of an applied electric or magnetic field produces an isotropic liquid crystal elastomer. Curing the second polymer layer 376 in the presence of an electrical field produces a nematic liquid crystalline elastomer.

In another embodiment, the top and bottom layers of the lens consist of nematic liquid crystal elastomers with directors that differ from each other. The resulting lens appears dark. An electrode array positioned in between the layers can be used to dynamically modulate optically transparent patterns on the lens.

In one aspect, first polymer layer 308 of the contact lens comprises a first liquid crystal elastomers prepared from a first pre-polymer that was cured while orienting the mesogens with an electric or magnetic field, resulting in a nematically oriented layer. Once the structure 314 is placed on the cured first polymer layer 308 as previously described, the second polymer layer 376 comprising a second liquid crystal elastomer is prepared by layering a second pre-polymer on the structure 314 and first polymer layer 308 then applying the electric or magnetic field at an angle that is 45 or 90 degrees oriented to the direction of the first layer as the pre-polymer polymerizes. The resulting second polymer layer 376 has a nematic ordering that differs from the far-field director from the first polymer layer 308. When an electrical field is applied to the body-mountable device, the ordering of the mesogens of the first and second polymer layers are changed. When an electrical field is applied to the completed contact lens, the mesogens in the first and second polymer layers re-orient themselves from an passive, inactive state to an active state as a result of the applied electrical field, thus changing the amount of light that can pass through the cornea.

In one representative example, a contact lens is fabricated such that the second polymer layer 376 (corresponding to the top of the lens) and the first polymer layer 308 of the lens (corresponding to the bottom of the lens) contain liquid crystal elastomers with far field directors that are oriented 45, 90, or 180 degrees (or another angle) with respect to each other. The first polymer layer 308 may be molded as previously described from pre-polymer material against any suitable form or substrate that regulates the shape and dimensions. Polymerization may be performed using any suitable agent such as heat or UV light in the presence of an oriented external magnetic or electric field to create a nematic liquid crystalline elastomer with a far field director. To create the second polymer layer 376 of the lens containing a nematic arrangement of the mesogens, molecular alignment of the mesogens is induced during polymer curing using an externally applied electric or magnetic field. The far field director of this liquid crystalline elastomer layer is oriented 45, 90, or 180 degrees (or another angle) with respect to the far field director of layer 308. Structure 314 is mounted on the first polymer layer 308 of lens as described previously. The first polymer layer 308 of lens having the structure 314 is positioned onto a second mold as previously described and pre-polymer material is added to form the second polymer layer 376 of the lens to enclose the structure 314 and form the completed contact lens. The second polymer layer 376 of the lens is cured thermally or by UV in the presence of an oriented external magnetic or electric field. Incorporation of electrodes in the electronic-containing layer or on one or more of the outer lens surfaces provides a mechanism for actively switching the alignment of the mesogens and controlling the orientation and polarization of light that passes through the lens to the eye. The resulting lens may be a dark color in its passive, inactive (unstimulated) state and become transparent in its active (stimulated) state.

In another embodiment, the first polymer layer 308 of the contact lens comprises a first liquid crystal elastomer prepared from pre-polymer material that was cured without orienting the mesogens with an applied electric or magnetic field, resulting in an isotropically oriented liquid crystalline elastomer layer. Once the structure 314 is placed on the first polymer layer 308 as previously described, the second polymer layer comprising a second liquid crystal elastomer may be prepared by layering pre-polymer material on the structure 314 and first polymer layer 308 then curing the polymer without orienting the mesogens with an electric or magnetic field, resulting in an isotropically oriented second polymer layer 376. The resulting contact lens may be transparent in its passive (unstimulated, non-polarized) state and a dark color (polarized) in its active (stimulated) state when an electric field is applied. The unstimulated state permits light of all orientations to be transmitted while the stimulated state only allows plane-polarized light to be transmitted to the eye.

In one representative example of this embodiment, a contact lens is fabricated such that the second polymer layer 376 (corresponding to the top part of the contact lens) and the first polymer layer 308 of the contact lens (corresponding to the bottom part of the contact lens facing the user) contain liquid crystal elastomers that are isotropic and do not contain molecular organization in any particular dimension. The first polymer layer 308 is molded as previously described from liquid crystal elastomers pre-polymer against any suitable form or substrate that regulates the shape and dimensions of the contact lens layer. Polymerization may be performed using a thermal or UV curing step. To create a first polymer layer 308 of the contact lens containing an isotropic arrangement of the liquid crystal elastomers mesogens, no molecular alignment is induced during curing (e.g., no external electric or magnetic field is applied) which would otherwise orient the mesogens in a specific orientation (e.g. far field director) as the polymer cures. The structure 314 is mounted on the first polymer layer 308 of lens as described previously. The first polymer layer 308 of the contact lens including structure 314 is positioned in a second mold and a pre-polymer material is added to form the second polymer layer 376 of the contact lens and enclose the structure 314 and form the completed body-mountable device as a contact lens. The second polymer layer 376 of the contact lens can either be cured thermally or by UV in the absence of an external electric or magnetic field, which would yield an isotropic liquid crystal elastomer. Incorporation of electrodes in the structure 314 or on one or more of the out contact lens surfaces provides a mechanism for actively switching the alignment of the mesogens and controlling the orientation and polarization of light that passes through the lens to the eye. The resulting lens may be transparent in its passive (unstimulated state) and darker (polarized) in its active, stimulated state. The inactive (unstimulated) state permits light with all orientations to be transmitted while the active (stimulated) state only allows plane-polarized light to be transmitted to the eye.

In one embodiment, electrodes or electrode arrays such as a grid of thin, overlapping metallic wires may be positioned on the surface of the first polymer layer 308 of the contact lens. The first or second polymer liquid crystalline elastomer layers of the device are isotropic. Application of a local current to the electrode grid and a second electrode located at either the outer or inner surface of layers 308 or 376 creates an optically 'dark' (polarized) feature. In this way, the lens can dynamically create patterns of dark features in the lens, the dimensions of which are dictated by the dimensions between the electrodes.

In one aspect, if both polymer layers are nematic and the far field directors are aligned with a relative orientation that differs by 90 degrees, the lens will appear dark. Application of a point electric field may create an optically "clear" pixel that permits unpolarized light to be transmitted through the pixel.

In another aspect, if one polymer layer is isotropic and the other is nematic, application of the current to the isotropic layer to align the liquid crystal mesogens along a far field director that is oriented 90 degrees with respect to the director in the nematic layer creates a dark "pixel". Either layer 308 or 376 could be nematic; the other layer then would be isotropic In another embodiment, the electrodes can be positioned in the same plane as structure 314. The electrodes may have a variety of shapes and dimensions, e.g., semi-circular, slightly curved, linear, curvilinear, or square. Applying a voltage across the electrodes switches the orientation of the mesogens in close proximity to the electrodes. Additional electrodes can be positioned on either the outside or inside surface of either layer 308 or 376.

In another embodiment, one electrode is positioned in the same plane as the structure 314 and a second electrode is positioned on the outer surface of the second polymer layer 376.

In another embodiment, one electrode is positioned in the same plane as structure 314 and a second electrode is positioned on the outer surface of the first polymer layer 308 of the contact lens.

In another embodiment, one electrode is positioned on the outer surface of the second polymer layer 376 of the contact lens and a second electrode is positioned at the outer surface of the first polymer layer 308 of the contact lens.

As mentioned above, a body-mountable device may be formed using the example methods described above. Further, the body-mountable device may be configured to monitor health-related information based on at least one analyte detected in a fluid of a user wearing the body-mountable device. An eye-mountable device configured to monitor health-related information based on at least one analyte detected from an eye of a user is described in greater detail below with reference to FIGS. 4 and 5a-5d.

A structure in accordance with an example embodiment may include a sensor, electronics, and an antenna all situated on a substrate. The electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior edge of the eye-mountable device. The sensor can generate an output signal indicative of a concentration of an analyte that the sensor receives via the channel.

Figure 4:
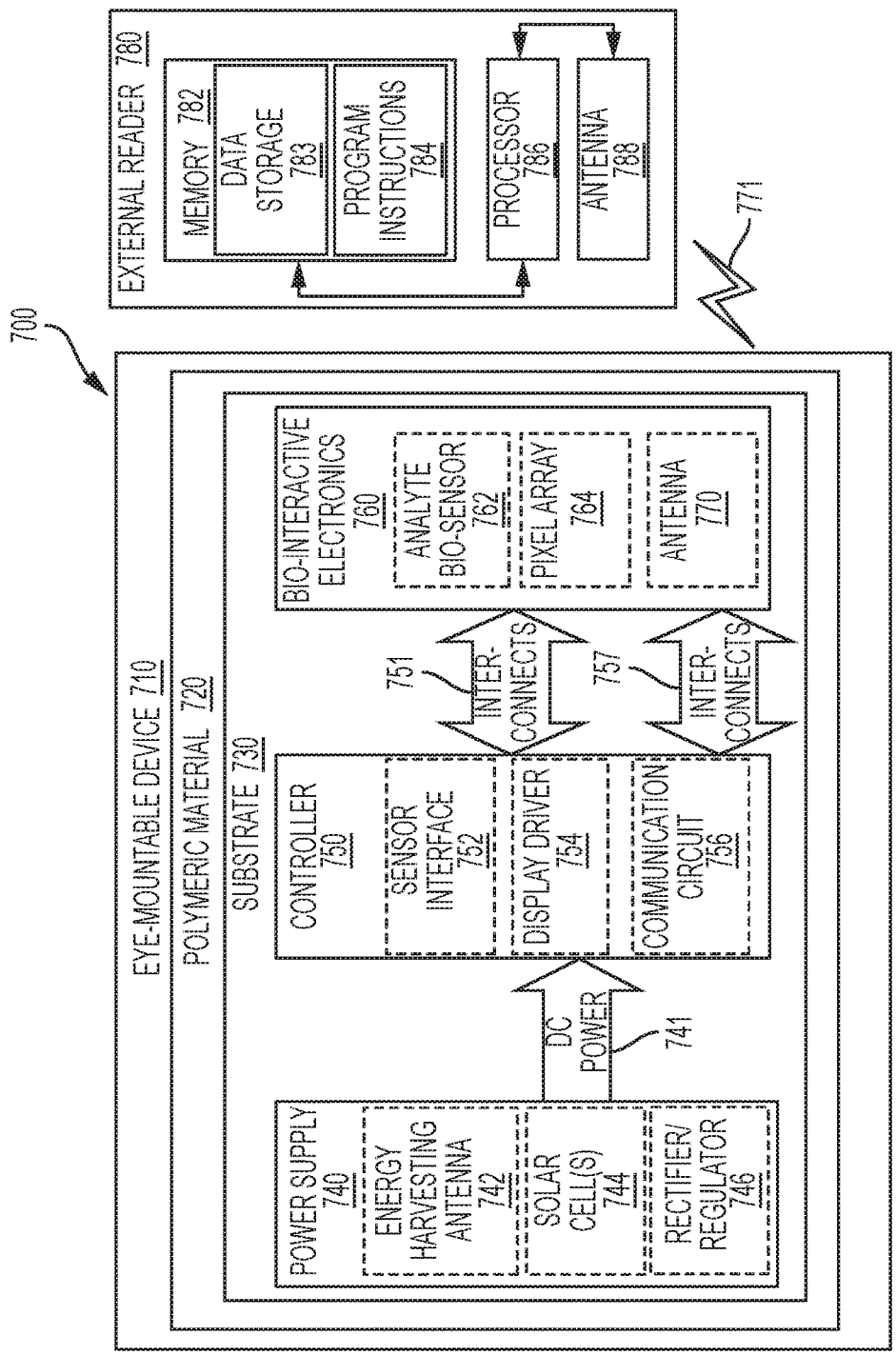
FIG. 4 is a block diagram of a system with an eye-mountable device in wireless communication with an external reader, according to an example embodiment.

FIG. 4 is a block diagram of a system 700 with an eye-mountable device 710 in wireless communication with an external reader 780. The exposed regions of the eye-mountable device 710 are made of a polymeric material 720 formed to be contact-mounted to a corneal surface of an eye. In accordance with the exemplary methods, polymeric material 720 may comprise a first polymer layer 308 and a second polymer layer 376.

Substrate 730 is embedded in the polymeric material 720 to provide a mounting surface for a power supply 740, a controller 750, bio-interactive electronics 760, and an antenna 770. The bio-interactive electronics 760 are operated by the controller 750. The power supply 740 supplies operating voltages to the controller 750 and/or the bio-interactive electronics 760. The antenna 770 is operated by the controller 750 to communicate information to and/or from the eye-mountable device 710. The antenna 770, the controller 750, the power supply 740, and the bio-interactive electronics 760 can all be situated on the embedded substrate 730. Because the eye-mountable device 710 includes electronics and is configured to be contact-mounted to an eye, it may also be referred to as an ophthalmic electronics platform.

To facilitate contact-mounting, the polymeric material 720 can have a concave surface configured to adhere ("mount") to a moistened corneal surface (e.g., by capillary forces with a tear film coating the corneal surface). Additionally or alternatively, the eye-mountable device 710 can be adhered by a vacuum force between the corneal surface and the polymeric material due to the concave curvature. While mounted with the concave surface against the eye, the anterior or outward-facing surface of the polymeric material 720 can have a convex curvature that is formed to not interfere with eye-lid motion while the eye-mountable device 710 is mounted to the eye. For example, the polymeric material 720 can be a substantially transparent curved polymeric disk shaped similarly to a contact lens.

The polymeric material 720 can include one or more bio-compatible materials, such as those employed for use in contact lenses or other ophthalmic applications involving direct contact with the corneal surface. The polymeric material 720 can optionally be formed in part from such bio-compatible materials or can include an outer coating with such bio-compatible materials. The polymeric material 720 can include materials configured to moisturize the corneal surface, such as hydrogels and the like. In some instances, the polymeric material 720 can be a deformable ("non-rigid") material to enhance wearer comfort. In some instances, the polymeric material 720 can be shaped to provide a predetermined, vision-correcting optical power, such as can be provided by a contact lens.

The substrate 730 includes one or more surfaces suitable for mounting the bio-interactive electronics 760, the controller 750, the power supply 740, and the antenna 770. The substrate 730 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 730 to form circuitry, electrodes, etc. For example, the antenna 770 can be formed by depositing a pattern of gold or another conductive material on the substrate 730. Similarly, interconnects 751, 757 between the controller 750 and the bio-interactive electronics 760, and between the controller 750 and the antenna 770, respectively, can be formed by depositing suitable patterns of conductive materials on the substrate 730. A combination of resists, masks, and deposition techniques can be employed to pattern materials on the substrate 730.

The substrate 730 can be a relatively rigid polymeric material, such as PET, paralyene or another material sufficient to structurally support the circuitry and/or electronics within the polymeric material 720. The eye-mountable device 710 can alternatively be arranged with a group of unconnected substrates rather than a single substrate. For example, the controller 750 and a bio-sensor or other bio-interactive electronic component can be mounted to one substrate, while the antenna 770 is mounted to another substrate and the two can be electrically connected via the interconnects 757.

In some embodiments, the bio-interactive electronics 760 (and the substrate 730) can be positioned away from the center of the eye-mountable device 710 and thereby avoid interference with light transmission to the eye through the center of the eye-mountable device 710. For example, where the eye-mountable device 710 is shaped as a concave-curved disk, the substrate 730 can be embedded around the periphery (e.g., near the outer circumference) of the disk. In some embodiments, the bio-interactive electronics 760 (and the substrate 730) can be positioned in the center region of the eye-mountable device 710. The bio-interactive electronics 760 and/or the substrate 730 can be substantially transparent to incoming visible light to mitigate interference with light transmission to the eye. Moreover, in some embodiments, the bio-interactive electronics 760 can include a pixel array 764 that emits and/or transmits light to be perceived by the eye according to display driver instructions. Thus, the bio-interactive electronics 760 can optionally be positioned in the center of the eye-mountable device so as to generate perceivable visual cues to a wearer of the eye-mountable device 710, such as by displaying information via the pixel array 764.

The substrate 730 can be shaped as a flattened ring with a radial width dimension sufficient to provide a mounting platform for the embedded electronics components. The substrate 730 can have a thickness sufficiently small to allow the substrate 730 to be embedded in the polymeric material 720 without influencing the profile of the eye-mountable device 710. The substrate 730 can have a thickness sufficiently large to provide structural stability suitable for supporting the electronics mounted thereon. For example, the substrate 730 can be shaped as a ring with a diameter of about 10 millimeters, a radial width of about 1 millimeter (e.g., an outer radius 1 millimeter larger than an inner radius), and a thickness of about 50 micrometers. The substrate 730 can optionally be aligned with the curvature of the anterior side of the eye-mountable device.

The power supply 740 is configured to harvest ambient energy to power the controller 750 and bio-interactive electronics 760. For example, a radio-frequency energy harvesting antenna 742 can capture energy from incident radio radiation. Additionally or alternatively, solar cell(s) 744 ("photovoltaic cells") can capture energy from incoming ultraviolet, visible, and/or infrared radiation. Furthermore, an inertial power scavenging system can be included to capture energy from ambient vibrations. The energy harvesting antenna 742 can optionally be a dual-purpose antenna that is also used to communicate information to the external reader 780. That is, the functions of the antenna 770 and the energy harvesting antenna 742 can be accomplished with the same physical antenna.

A rectifier/regulator 746 can be used to condition the captured energy to a stable DC supply voltage 741 that is supplied to the controller 750. For example, the energy harvesting antenna 742 can receive incident radio frequency radiation. Varying electrical signals on the leads of the antenna 742 are output to the rectifier/regulator 746. The rectifier/regulator 746 rectifies the varying electrical signals to a DC voltage and regulates the rectified DC voltage to a level suitable for operating the controller 750. Additionally or alternatively, output voltage from the solar cell(s) 744 can be regulated to a level suitable for operating the controller 750. The rectifier/regulator 746 can include one or more energy storage devices arranged to mitigate high frequency variations in the ambient energy harvesting antenna 742 and/or solar cell(s) 744. For example, an energy storage device (e.g., capacitor, inductor, etc.) can be connected to the output of the rectifier/regulator 746 so as to function as a low-pass filter.

The controller 750 is turned on when the DC supply voltage 741 is provided to the controller 750, and the logic in the controller 750 operates the bio-interactive electronics 760 and the antenna 770. The controller 750 can include logic circuitry configured to operate the bio-interactive electronics 760 so as to interact with a biological environment of the eye-mountable device 710. The interaction could involve the use of one or more components, such as an analyte bio-sensor 762, in bio-interactive electronics 760 to obtain input from the biological environment. Alternatively or additionally, the interaction could involve the use of one or more components, such as the pixel array 764, to provide an output to the biological environment.

In one example, a sensor interface module 752 can be included for operating the analyte bio-sensor 762. The analyte bio-sensor 762 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 752 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOX") can be situated around the working electrode to catalyze glucose into hydrogen peroxide ($H_2O_2$). The hydrogen peroxide can then be oxidized at the working electrode, which releases electrons to the working electrode, which generates a current.

$$glucose + O_2 \rightarrow H_2O_2 + gluconolactone$$

$$H_2O_2 \rightarrow 2H^+ + O_2 \pm 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 750 can optionally include a display driver module 754 for operating the pixel array 764. The pixel array 764 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 754. Such a pixel array 764 can also optionally include more than one color of pixels (e.g., red, green, and blue pixels) to render visual content in color. The display driver module 754 can include, for example, one or more data lines providing programming information to the separately programmed pixels in the pixel array 764 and one or more addressing lines for setting groups of pixels to receive such programming information. Such a pixel array 764 situated on the eye can also include one or more lenses to direct light from the pixel array to a focal plane perceivable by the eye.

The controller 750 can also include a communication circuit 756 for sending and/or receiving information via the antenna 770. The communication circuit 756 can optionally include one or more oscillators, mixers, frequency injectors, etc. to modulate and/or demodulate information on a carrier frequency to be transmitted and/or received by the antenna 770. In some examples, the eye-mountable device 710 is configured to indicate an output from a bio-sensor by modulating an impedance of the antenna 770 in a manner that is perceivable by the external reader 780. For example, the communication circuit 756 can cause variations in the amplitude, phase, and/or frequency of backscatter radiation from the antenna 770, and such variations can be detected by the external reader 780.

The controller 750 is connected to the bio-interactive electronics 760 via interconnects 751. For example, where the controller 750 includes logic elements implemented in an integrated circuit to form the sensor interface module 752 and/or display driver module 754, a patterned conductive material (e.g., gold, platinum, palladium, titanium, copper, aluminum, silver, metals, combinations of these, etc.) can connect a terminal on the chip to the bio-interactive electronics 760. Similarly, the controller 750 is connected to the antenna 770 via interconnects 757.

It is noted that the block diagram shown in FIG. 4 is described in connection with functional modules for convenience in description. However, embodiments of the eye-mountable device 710 can be arranged with one or more of the functional modules ("sub-systems") implemented in a single chip, integrated circuit, and/or physical feature. For example, while the rectifier/regulator 746 is illustrated in the power supply block 740, the rectifier/regulator 746 can be implemented in a chip that also includes the logic elements of the controller 750 and/or other features of the embedded electronics in the eye-mountable device 710. Thus, the DC supply voltage 741 that is provided to the controller 750 from the power supply 740 can be a supply voltage that is provided on a chip by rectifier and/or regulator components of the same chip. That is, the functional blocks in FIG. 4 shown as the power supply block 740 and controller block 750 need not be implemented as separated modules. Moreover, one or more of the functional modules described in FIG. 4 can be implemented by separately packaged chips electrically connected to one another.

Additionally or alternatively, the energy harvesting antenna 742 and the antenna 770 can be implemented with the same physical antenna. For example, a loop antenna can both harvest incident radiation for power generation and communicate information via backscatter radiation.

The external reader 780 includes an antenna 788 (or group of more than one antennae) to send and receive wireless signals 771 to and from the eye-mountable device 710. The external reader 780 also includes a computing system with a processor 786 in communication with a memory 782. The memory 782 is a non-transitory computer-readable medium that can include, without limitation, magnetic disks, optical disks, organic memory, and/or any other volatile (e.g., RAM) or non-volatile (e.g., ROM) storage system readable by the processor 786. The memory 782 can include a data storage 783 to store indications of data structures, such as sensor readings (e.g., from the analyte bio-sensor 762), program settings (e.g., to adjust behavior of the eye-mountable device 710 and/or external reader 780), etc. The memory can also include program instructions 784 for execution by the processor 786 to cause the external reader to perform processes specified by the program instructions 784. For example, the program instructions 784 can cause external reader 780 to provide a user interface that allows for retrieving information communicated from the eye-mountable device 710 (e.g., sensor outputs from the analyte bio-sensor 762). The external reader 780 can also include one or more hardware components for operating the antenna 788 to send and receive the wireless signals 771 to and from the eye-mountable device 710. For example, oscillators, frequency injectors, encoders, decoders, amplifiers, filters, etc. can drive the antenna 788 according to instructions from the processor 786.

The external reader 780 can be a smart phone, digital assistant, or other portable computing device with wireless connectivity sufficient to provide the wireless communication link 771. The external reader 780 can also be implemented as an antenna module that can be plugged in to a portable computing device, such as in an example where the communication link 771 operates at carrier frequencies not commonly employed in portable computing devices. In some instances, the external reader 780 is a special-purpose device configured to be worn relatively near a wearer's eye to allow the wireless communication link 771 to operate with a low power budget. For example, the external reader 780 can be integrated in eyeglasses, integrated in a piece of jewelry such as a necklace, earring, etc., or integrated in an article of clothing worn near the head, such as a hat, headband, etc.

In an example where the eye-mountable device 710 includes an analyte bio-sensor 762, the system 700 can be operated to monitor the analyte concentration in tear film on the surface of the eye. Thus, the eye-mountable device 710 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 700 configured as a tear film analyte monitor, the external reader 780 can emit radio frequency radiation 771 that is harvested to power the eye-mountable device 710 via the power supply 740. Radio frequency electrical signals captured by the energy harvesting antenna 742 (and/or the antenna 770) are rectified and/or regulated in the rectifier/regulator 746 and a regulated DC supply voltage 741 is provided to the controller 750. The radio frequency radiation 771 thus turns on the electronic components within the eye-mountable device 710. Once turned on, the controller 750 operates the analyte bio-sensor 762 to measure an analyte concentration level. For example, the sensor interface module 752 can apply a voltage between a working electrode and a reference electrode in the analyte bio-sensor 762 sufficient to cause the analyte to undergo an electrochemical reaction at the working electrode. The current through the working electrode can be measured to provide the sensor output indicative of the analyte concentration. The controller 750 can operate the antenna 770 to communicate the sensor results back to the external reader 780 (e.g., via the communication circuit 756). The sensor result can be communicated by, for example, modulating an impedance of the antenna 770 such that the modulation in impedance is detected by the external reader 780. The modulation in antenna impedance can be detected by, for example, backscatter radiation from the antenna 770.

In some embodiments, the system 700 can operate to non-continuously ("intermittently") supply energy to the eye-mountable device 710 to power the on-board controller 750 and electronics 760. For example, radio frequency radiation 771 can be supplied to power the eye-mountable device 710 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 771 can be considered an interrogation signal from the external reader 780 to the eye-mountable device 710 to request a measurement. By periodically interrogating the eye-mountable device 710 (e.g., by supplying radio frequency radiation 771 to temporarily turn the device on) and storing the sensor results (e.g., via the data storage 783), the external reader 780 can accumulate a set of analyte concentration measurements over time without continuously powering the eye-mountable device 710.

FIG. 5*a* is a top view of an eye-mountable electronic device 810. FIG. 5*b* is a side view of the eye-mountable electronic device shown in FIG. 5*a*. It is noted that relative dimensions in FIGS. 5*a* and 5*b* are not necessarily to scale, but have been rendered for purposes of explanation only in describing the arrangement of the eye-mountable electronic device 810. The eye-mountable device 810 is formed of a polymeric material 820 shaped as a curved disk. The polymeric material 820 can be a substantially transparent material to allow incident light to be transmitted to the eye while the eye-mountable device 810 is mounted to the eye. The polymeric material 820 can be a bio-compatible material similar to those employed to form vision correction and/or cosmetic contact lenses in optometry, such as PET, polymethyl methacrylate ("PMMA"), silicone hydrogels, combinations of these, etc. The polymeric material 820 can be formed with one side having a concave surface 826 suitable to fit over a corneal surface of an eye. The opposing side of the disk can have a convex surface 824 that does not interfere with eyelid motion while the eye-mountable device 810 is mounted to the eye. A circular outer side edge 828 connects the concave surface 824 and convex surface 826.

The eye-mountable device 810 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 810 can be selected according to the size and/or shape of the corneal surface and/or the scleral surface of the wearer's eye.

While the eye-mountable device 810 is mounted in an eye, the convex surface 824 (i.e., the anterior surface) faces outward to the ambient environment while the concave surface 826 (i.e., the posterior surface) faces inward, toward the corneal surface. The convex surface 824 can therefore be considered an outer, top surface of the eye-mountable device 810 whereas the concave surface 826 can be considered an inner, bottom surface. The "top" view shown in FIG. 5*a* is facing the convex surface 824.

A substrate 830 is embedded in the polymeric material 820. The substrate 830 can be embedded to be situated along the outer periphery 822 of the polymeric material 820, away from the center region 821. The substrate 830 does not interfere with vision because it is too close to the eye to be in focus and is positioned away from the center region 821 where incident light is transmitted to the light-sensing portions of the eye. Moreover, the substrate 830 can be formed of a transparent material to further mitigate any effects on visual perception.

The substrate 830 can be shaped as a flat, circular ring (e.g., a disk with a central hole). The flat surface of the substrate 830 (e.g., along the radial width) is a platform for mounting electronics such as chips (e.g., via flip-chip mounting) and for patterning conductive materials (e.g., via deposition techniques) to form electrodes, antenna(e), and/or connections. The substrate 830 and the polymeric material 820 can be approximately cylindrically symmetric about a common central axis. The substrate 830 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 830 can be implemented in a variety of different form factors.

A loop antenna 870, a controller 850, and bio-interactive electronics 860 are disposed on the embedded substrate 830. The controller 850 can be a chip including logic elements configured to operate the bio-interactive electronics 860 and the loop antenna 870. The controller 850 is electrically connected to the loop antenna 870 by interconnects 857 also situated on the substrate 830. Similarly, the controller 850 is electrically connected to the bio-interactive electronics 860 by interconnects 851. The interconnects 851, 857, the loop antenna 870, and any conductive electrodes (e.g., for an electrochemical analyte bio-sensor, etc.) can be formed from conductive materials patterned on the substrate 830 by a process for precisely patterning such materials, such as deposition or lithography. The conductive materials patterned on the substrate 830 can be, for example, gold, platinum, palladium, titanium, carbon, aluminum, copper, silver, silver-chloride, and/or other materials.

With reference to FIG. 5*a*, which is a view facing the convex surface 824 of the eye-mountable device 810, the bio-interactive electronics 860 is mounted to a side of the substrate 830 facing the convex surface 824. Where the bio-interactive electronics 860 includes an analyte bio-sensor, for example, mounting such a bio-sensor on the substrate 830 facing the convex surface 824 allows the bio-sensor to receive analyte concentrations in tear film through a channel 872 in the polymeric material 820 to the convex surface 824 (as illustrated in FIGS. 5*c* and 5*d*). In some embodiments, some electronic components can be mounted on one side of the substrate 830, while other electronic components are mounted to the opposing side, and connections between the two can be made through conductive materials passing through the substrate 830.

The loop antenna 870 is a layer of conductive material patterned along the flat surface of the substrate to form a flat conductive ring. In some instances, the loop antenna 870 can be formed without making a complete loop. For instance, the loop antenna 870 can have a cutout to allow room for the controller 850 and the bio-interactive electronics 860, as illustrated in FIG. 5*a*. However, the loop antenna 870 can also be arranged as a continuous strip of conductive material that wraps entirely around the flat surface of the substrate 830 one or more times. For example, a strip of conductive material with multiple windings can be patterned on the side of the substrate 830 opposite the controller 850 and bio-interactive electronics 860. Interconnects between the ends of such a wound antenna (e.g., the antenna leads) can be passed through the substrate 830 to the controller 850. In some embodiments, the loop antenna can include a plurality of conductive loops spaced apart from each other, such as three conductive loops, five conductive loops, nine conductive loops, etc. With such an arrangement, the polymeric material 820 may extend between adjacent conductive loops in the plurality of conductive loops.

FIG. 5*c* is a side cross-section view of the eye-mountable electronic device 810 while mounted to a corneal surface 884 of an eye 880. FIG. 5*d* is a close-up side cross-section view enhanced to show tear film layers 890, 892 surrounding the exposed surfaces 824, 826 of the eye-mountable device 810. It is noted that relative dimensions in FIGS. 5*c* and 8*d* are not necessarily to scale, but have been rendered for purposes of explanation only in describing the arrangement of the eye-mountable electronic device 810. For example, the total thickness of the eye-mountable device 810 can be about 200 micrometers, while the thickness of the tear film layers 890, 892 can each be about 10 micrometers, although this ratio may not be reflected in the drawings. Some aspects are exaggerated to allow for illustration and facilitate explanation.

The eye 880 includes a cornea 882 that is covered by bringing the upper eyelid 886 and lower eyelid 888 together over the top of the eye 880. Incident light is received by the eye 880 through the cornea 882, where light is optically directed to light sensing elements of the eye 880 (e.g., rods and cones, etc.) to stimulate visual perception. The motion of the eyelids 886, 888 distributes a tear film across the exposed corneal surface 884 of the eye 880. The tear film is an aqueous solution secreted by the lacrimal gland to protect and lubricate the eye 880. When the eye-mountable device 810 is mounted in the eye 880, the tear film coats both the convex and concave surfaces 824, 826 with an inner layer 890 (along the concave surface 826) and an outer layer 892 (along the convex layer 824). The tear film layers 890, 892 can be about 10 micrometers in thickness and together account for about 10 microliters.

The tear film layers 890, 892 are distributed across the corneal surface 884 and/or the convex surface 824 by motion of the eyelids 886, 888. For example, the eyelids 886, 888 raise and lower, respectively, to spread a small volume of tear film across the corneal surface 884 and/or the convex surface 824 of the eye-mountable device 810. The tear film layer 890 on the corneal surface 884 also facilitates mounting the eye-mountable device 810 by capillary forces between the concave surface 826 and the corneal surface 884. In some embodiments, the eye-mountable device 810 can also be held over the eye in part by vacuum forces against the corneal surface 884 due to the concave curvature of the eye-facing concave surface 826.

As shown in the cross-sectional views in FIGS. 5*c* and 5*d*, the substrate 830 can be inclined such that the flat mounting surfaces of the substrate 830 are approximately parallel to the adjacent portion of the convex surface 824. As described above, the substrate 830 is a flattened ring with an inward-facing surface 832 (facing the concave surface 826 of the polymeric material 820) and an outward-facing surface 834 (facing the convex surface 824). The substrate 830 can have electronic components and/or patterned conductive materials mounted to either or both mounting surfaces 832, 834.

As shown in FIG. 5*d*, the bio-interactive electronics 860, the controller 850, and the conductive interconnect 851 are located between the outward-facing surface 834 and the inward-facing surface 832 such that the bio-interactive electronics 860 are facing the convex surface 824. As described above, the polymer layer defining the anterior side may be greater than 50 micrometers thick, whereas the polymer layer defining the posterior side may be less than 150 micrometers. Thus, the bio-interactive electronics 860 may be at least 50 micrometers away from the convex surface 824 and may be a greater distance away from the concave surface 826. However, in other examples, the bio-interactive electronics 860 may be mounted on the inward-facing surface 832 of the substrate 830 such that the bio-interactive electronics 860 are facing the concave surface 826. The bio-interactive electronics 860 could also be positioned closer to the concave surface 826 than the convex surface 824. With this arrangement, the bio-interactive electronics 860 can receive analyte concentrations in the tear film 892 through the channel 872.

While the body-mountable device has been described as comprising the eye-mountable device 710 and/or the eye-mountable device 810, the body-mountable device could comprise other mountable devices that are mounted on or in other portions of the body.

As noted, in some embodiments, the body-mountable device may comprise a tooth-mountable device. In some embodiments, the tooth-mountable device may take the form of or be similar in form to the eye-mountable device 710 and/or the eye-mountable device 810. For instance, the tooth-mountable device may include a polymeric material that is the same or similar to any of the polymeric materials described herein and a substrate that is the same or similar to any of the substrates described herein.

As noted, in some embodiments, the body-mountable device may comprise a skin-mountable device. In some embodiments, the skin-mountable device may take the form of or be similar in form to the eye-mountable device 710 and/or the eye-mountable device 810. For instance, the skin-mountable device may include a polymeric material that is the same or similar to any of the polymeric materials described herein and a substrate that is the same or similar to any of the substrates described herein.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A body-mountable device comprising:
    a first polymer layer, the first polymer layer comprising a first liquid crystal elastomer;
    a structure on the first polymer layer, the structure comprising a sensor; and
    a second polymer layer over the first polymer layer and the structure, the second polymer layer comprises a second liquid crystal elastomer,
    wherein the first polymer layer defines a first side of a body-mountable device and the second polymer layer defines a second side of the body-mountable device opposite the first side, and
    wherein the application of an electric field across the first polymer layer and the second polymer layer causes the body-mountable device to polarize or depolarize in response to the electric field.

2. The body-mountable device of claim 1, wherein the body-mountable device is in the form of a contact lens.

3. The body-mountable device of claim 1, wherein one polymer layer is isotropically ordered and the remaining polymer layer is nematically ordered.

4. The body-mountable device of claim 1, wherein the first and second polymer layers are isotropically oriented.

5. The body-mountable device of claim 1, wherein the first and second polymer layers are nematically ordered.

6. The body-mountable device of claim 5, wherein the first or the second polymer layer is nematically ordered with a far field director at an angle that is oriented 45, 90, or 180 degrees to the far field director of the remaining polymer layer.

7. The body-mountable device of claim 1, wherein the first and second liquid crystal elastomers comprise a silicon-based polymer having mesogens with a dipole moment.

8. The body-mountable device of claim 1, wherein the first polymer layer, the second polymer layer, or both have a pre-determined orientation.

9. A contact lens comprising:
    a first polymer layer, the first polymer layer comprising a first liquid crystal elastomer;
    a structure on the first polymer layer, the structure comprising a sensor; and
    a second polymer layer over the first polymer layer and the structure, the second polymer layer comprising a second liquid crystal elastomer,
    wherein the first polymer layer, the second polymer layer, or both are formed by polymerization of a liquid crystal pre-polymer in the presence of an electric or magnetic field, and
    wherein the application of an electric field across the first polymer layer and the second polymer layer causes the contact lens to polarize or depolarize in response to the electric field.

10. The contact lens of claim 9, wherein a structure is positioned on the first polymer layer prior to forming the second polymer layer.

11. The contact lens of claim 10, wherein the structure further comprises an electronic component.

12. The contact lens of claim 9, wherein one polymer layer is isotropically ordered and the remaining polymer layer is nematically ordered.

13. The contact lens of claim 9, wherein the first and second polymer layers are isotropically oriented.

14. The contact lens of claim 9, wherein the first and second polymer layers are nematically ordered.

15. The contact lens of claim 14, wherein the first or the second polymer layer is nematically ordered with a far field director at an angle that is oriented 45, 90, or 180 degrees to the far field director of the remaining polymer layer.

16. The contact lens of claim 9, wherein the first and second liquid crystal elastomers comprise a silicon-based polymer having mesogens with a dipole moment.

17. The contact lens of claim 9, wherein the first polymer layer, the second polymer layer, or both have a pre-determined orientation.

18. The contact lens of claim 9, further comprising electrodes for generating an applied electrical field across the first polymer layer and second polymer layer to polarize or depolarize each polymer layer.

* * * * *